（12）United States Patent
Costella et al.

(10) Patent No.: US 10,881,818 B2
(45) Date of Patent: Jan. 5, 2021

(54) SMART OSCILLATING POSITIVE EXPIRATORY PRESSURE DEVICE

(71) Applicant: TRUDELL MEDICAL INTERNATIONAL, London (CA)

(72) Inventors: Stephen Costella, London (CA); Alanna Kirchner, London (CA); Robert Morton, London (CA); Adam Meyer, London (CA); Peter Scarrott, London (CA)

(73) Assignee: Trudell Medical International, London (CA)

( * ) Notice: Subject to any disclaimer, the term of this patent is extended or adjusted under 35 U.S.C. 154(b) by 267 days.

(21) Appl. No.: 15/644,138

(22) Filed: Jul. 7, 2017

(65) Prior Publication Data
US 2018/0008790 A1    Jan. 11, 2018

Related U.S. Application Data

(60) Provisional application No. 62/359,970, filed on Jul. 8, 2016.

(51) Int. Cl.
A61M 16/00    (2006.01)
A61B 5/087    (2006.01)
(Continued)

(52) U.S. Cl.
CPC ....... A61M 16/0006 (2014.02); A61B 5/0876 (2013.01); A61M 16/0009 (2014.02);
(Continued)

(58) Field of Classification Search
CPC .......... A61M 16/0006; A61M 2205/52; A61M 2205/505; A61M 2205/3584;
(Continued)

(56) References Cited

U.S. PATENT DOCUMENTS 4,984,158 A    1/1991    Hillsman
5,016,627 A *  5/1991    Dahrendorf ............ A62B 9/022
                                                128/204.29

(Continued)

FOREIGN PATENT DOCUMENTS

CA    2 607 458 A1    11/2006
DE    102010024912 B4    2/2013
(Continued)

OTHER PUBLICATIONS

PCT Notification of the International Search Report and Written Opinion of the International Search Authority dated Jan. 5, 2018, 10 pgs.

Primary Examiner — Joseph D. Boecker
(74) Attorney, Agent, or Firm — Brinks Gilson & Lione

(57) ABSTRACT

An oscillating positive expiratory pressure system including an oscillating positive expiratory pressure device having a chamber, an input component in communication with the chamber, wherein the input component is operative to sense a flow and/or pressure and generate an input signal correlated to the flow or pressure, a processor operative to receive the input signal from the input component and generate an output signal, and an output component operative to receive the output signal, and display an output.

26 Claims, 24 Drawing Sheets

(51) Int. Cl.
*A61M 16/20* (2006.01)
*G01F 1/00* (2006.01)

(52) U.S. Cl.
CPC ... *A61M 16/021* (2017.08); *A61B 2562/0219* (2013.01); *A61M 16/024* (2017.08); *A61M 16/202* (2014.02); *A61M 16/208* (2013.01); *A61M 2016/003* (2013.01); *A61M 2016/0027* (2013.01); *A61M 2016/0036* (2013.01); *A61M 2205/3334* (2013.01); *A61M 2205/3569* (2013.01); *A61M 2205/3584* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/583* (2013.01); *G01F 1/00* (2013.01)

(58) Field of Classification Search
CPC ........ A61M 2205/3334; A61M 16/024; A61M 2016/0027; A61M 2016/003; A61M 16/0003; A61M 16/0009; A61M 16/202; A61M 16/208; A61M 2016/0036; A61M 2016/0042; A61B 5/0876; A61B 2562/0219; G01F 1/00; G01F 1/34; G01F 1/52; G01F 3/22; G01F 3/224; G01F 3/225; G01F 3/227; G01F 15/16
See application file for complete search history.

(56) References Cited

U.S. PATENT DOCUMENTS

| | | | |
|---|---|---|---|
| 5,284,133 A | 2/1994 | Burns et al. | |
| 5,331,953 A | 7/1994 | Andersson et al. | |
| 5,333,106 A | 7/1994 | Lanpher et al. | |
| 5,363,842 A | 11/1994 | Mishelevich et al. | |
| 5,431,154 A | 7/1995 | Seigel et al. | |
| 5,477,849 A | 12/1995 | Fry | |
| 5,505,192 A | 4/1996 | Samiotes et al. | |
| 5,505,195 A | 4/1996 | Wolf et al. | |
| 5,758,638 A | 6/1998 | Kreamer | |
| 5,794,612 A | 8/1998 | Wachter et al. | |
| 5,809,997 A | 9/1998 | Wolf | |
| 5,819,726 A | 10/1998 | Rubsamen et al. | |
| 5,865,172 A | 2/1999 | Butler et al. | |
| 5,937,852 A | 8/1999 | Butler et al. | |
| 6,073,628 A | 6/2000 | Butler et al. | |
| 6,138,669 A | 10/2000 | Rocci, Jr. et al. | |
| 6,148,815 A | 11/2000 | Wolf | |
| 6,192,876 B1 | 2/2001 | Denyer et al. | |
| 6,202,642 B1 | 3/2001 | McKinnon et al. | |
| 6,234,167 B1 | 5/2001 | Cox et al. | |
| 6,358,058 B1 | 3/2002 | Strupat et al. | |
| 6,578,571 B1 | 6/2003 | Watt | |
| 6,651,651 B1 | 11/2003 | Bonney et al. | |
| 6,823,862 B2 | 11/2004 | McNaughton | |
| 6,839,604 B2 | 1/2005 | Godfrey et al. | |
| 6,880,722 B2 | 4/2005 | Anderson et al. | |
| 6,904,907 B2 | 6/2005 | Speldrich et al. | |
| 6,932,083 B2 | 8/2005 | Jones et al. | |
| 6,934,220 B1 | 8/2005 | Cruitt et al. | |
| 6,958,691 B1 | 10/2005 | Anderson et al. | |
| 6,990,975 B1 | 1/2006 | Jones et al. | |
| 7,009,517 B2 | 3/2006 | Wood | |
| 7,072,738 B2 | 7/2006 | Bonney et al. | |
| 7,089,786 B2 | 8/2006 | Walker | |
| 7,091,864 B2 | 8/2006 | Veitch et al. | |
| 7,151,456 B2 | 12/2006 | Godfrey | |
| 7,159,533 B1 | 1/2007 | Redd et al. | |
| 7,191,777 B2 | 3/2007 | Brand et al. | |
| 7,198,172 B2 | 4/2007 | Harvey et al. | |
| 7,233,228 B2 | 6/2007 | Lintell | |
| 7,331,340 B2 | 2/2008 | Barney | |
| 7,383,837 B2 | 6/2008 | Robertson et al. | |
| 7,424,888 B2 | 6/2008 | Harvey et al. | |
| 7,495,546 B2 | 2/2009 | Lintell | |
| 7,597,099 B2 | 10/2009 | Jones et al. | |
| 7,661,423 B2 | 2/2010 | Brand et al. | |
| 7,730,847 B1 | 6/2010 | Redd et al. | |
| 7,748,382 B2 | 7/2010 | Denyer et al. | |
| 7,819,116 B2 | 10/2010 | Brand et al. | |
| 7,837,648 B2 | 11/2010 | Blair et al. | |
| 8,165,892 B2 | 4/2012 | Carter et al. | |
| 8,261,738 B2 | 9/2012 | Denyer et al. | |
| 8,403,861 B2 | 3/2013 | Williams et al. | |
| 8,424,517 B2 | 4/2013 | Sutherland et al. | |
| 8,464,707 B2 | 6/2013 | Jongejan et al. | |
| 8,550,067 B2 | 10/2013 | Bruce et al. | |
| 8,607,783 B2 | 12/2013 | Takei et al. | |
| 8,671,943 B2* | 3/2014 | Shigematsu | A61M 16/06 128/205.25 |
| 8,807,131 B1 | 8/2014 | Tunnell et al. | |
| 9,035,765 B2 | 5/2015 | Engelhard et al. | |
| 9,072,846 B2 | 7/2015 | Helmlinger | |
| 9,242,056 B2 | 1/2016 | Andersen et al. | |
| D757,926 S | 5/2016 | Von Sickle et al. | |
| 9,352,107 B2 | 5/2016 | Von Hollen et al. | |
| 9,427,534 B2 | 8/2016 | Bruin et al. | |
| 9,452,317 B2 | 9/2016 | Arkush | |
| 9,468,729 B2 | 10/2016 | Sutherland et al. | |
| D771,800 S | 11/2016 | Engelhard et al. | |
| 9,764,104 B2 | 9/2017 | Gumaste et al. | |
| 9,782,551 B2 | 10/2017 | Morrison et al. | |
| 2002/0090601 A1 | 7/2002 | Strupat et al. | |
| 2002/0162399 A1* | 11/2002 | Esashi | G01L 9/0077 73/715 |
| 2003/0075171 A1 | 4/2003 | Jones et al. | |
| 2003/0159694 A1 | 8/2003 | McNaughton | |
| 2004/0007231 A1 | 1/2004 | Zhou | |
| 2004/0244797 A1* | 12/2004 | Jackson | A62B 9/027 128/205.24 |
| 2006/0089545 A1 | 4/2006 | Ratjen et al. | |
| 2007/0017506 A1 | 1/2007 | Bell et al. | |
| 2007/0125372 A1 | 6/2007 | Chen | |
| 2009/0194104 A1 | 8/2009 | Van Sickle | |
| 2009/0314292 A1 | 12/2009 | Overfield et al. | |
| 2010/0191192 A1 | 7/2010 | Prasad et al. | |
| 2010/0192948 A1 | 8/2010 | Sutherland et al. | |
| 2010/0250280 A1 | 9/2010 | Sutherland | |
| 2010/0252036 A1 | 10/2010 | Sutherland et al. | |
| 2010/0324439 A1 | 12/2010 | Davenport | |
| 2011/0180563 A1 | 7/2011 | Fitchett et al. | |
| 2011/0226237 A1 | 9/2011 | Morrison | |
| 2011/0226242 A1 | 9/2011 | Von Hollen et al. | |
| 2012/0012106 A1 | 1/2012 | Bari | |
| 2012/0165693 A1 | 6/2012 | Williams et al. | |
| 2012/0240923 A1 | 9/2012 | Denyer et al. | |
| 2012/0285236 A1 | 11/2012 | Haartsen et al. | |
| 2012/0291779 A1 | 11/2012 | Haartsen et al. | |
| 2012/0312302 A1 | 12/2012 | Cardelius et al. | |
| 2013/0008436 A1 | 1/2013 | Von Hollen et al. | |
| 2013/0053719 A1 | 2/2013 | Wekell | |
| 2013/0092158 A1 | 4/2013 | Levy et al. | |
| 2013/0151162 A1 | 6/2013 | Harris et al. | |
| 2013/0186392 A1 | 7/2013 | Haartsen et al. | |
| 2014/0000598 A1 | 1/2014 | Sutherland et al. | |
| 2014/0000599 A1 | 1/2014 | Dyche et al. | |
| 2014/0106324 A1 | 4/2014 | Adams et al. | |
| 2014/0182584 A1 | 7/2014 | Sutherland et al. | |
| 2014/0247155 A1* | 9/2014 | Proud | A61B 5/1118 340/870.16 |
| 2014/0257126 A1 | 9/2014 | Vink et al. | |
| 2014/0318534 A1 | 10/2014 | Engelbreth | |
| 2014/0352690 A1 | 12/2014 | Kolb et al. | |
| 2015/0011906 A1 | 1/2015 | Wallach | |
| 2015/0059739 A1 | 3/2015 | Aslam | |
| 2015/0061867 A1 | 3/2015 | Engelhard et al. | |
| 2015/0099994 A1 | 4/2015 | Spencer et al. | |
| 2015/0100276 A1 | 4/2015 | Huang et al. | |
| 2015/0100335 A1 | 4/2015 | Engelhard et al. | |
| 2015/0112707 A1 | 4/2015 | Manice et al. | |
| 2015/0122261 A1 | 5/2015 | Pettit | |
| 2015/0164373 A1 | 6/2015 | Davis et al. | |

(56) References Cited

U.S. PATENT DOCUMENTS

| | | | |
|---|---|---|---|
| 2015/0174348 A1 | 6/2015 | Tunnell et al. |
| 2015/0174349 A1 | 6/2015 | Tunnell et al. |
| 2015/0235548 A1 | 8/2015 | Engelhard et al. |
| 2015/0283337 A1 | 10/2015 | Adams et al. |
| 2015/0352281 A1 | 10/2015 | Pfrang |
| 2016/0045681 A1 | 2/2016 | Cheatham, III et al. |
| 2016/0045682 A1 | 2/2016 | Boyden et al. |
| 2016/0045683 A1 | 2/2016 | Cheatham, III et al. |
| 2016/0045685 A1 | 2/2016 | Hyde et al. |
| 2016/0051776 A1 | 2/2016 | Von Hollen |
| 2016/0058960 A1 | 3/2016 | Papania et al. |
| 2016/0082208 A1 | 3/2016 | Ballam et al. |
| 2016/0106375 A1 | 4/2016 | Leydon |
| 2016/0106935 A1 | 4/2016 | Sezan et al. |
| 2016/0129182 A1 | 5/2016 | Schuster et al. |
| 2016/0129206 A1 | 5/2016 | Engelbreth |
| 2016/0136366 A1 | 5/2016 | Bennett |
| 2016/0136367 A1 | 5/2016 | Varney |
| 2016/0144141 A1 | 5/2016 | Biwas et al. |
| 2016/0144142 A1 | 5/2016 | Baker et al. |
| 2016/0166766 A1 | 6/2016 | Schuster et al. |
| 2016/0184535 A1 | 6/2016 | Edwards et al. |
| 2016/0193436 A1 | 7/2016 | Khasawneh |
| 2016/0213868 A1 | 7/2016 | Khasawneh et al. |
| 2016/0256639 A1 | 9/2016 | Van Sickle et al. |
| 2016/0287139 A1 | 10/2016 | Luttrell |
| 2016/0314256 A1 | 10/2016 | Su et al. |
| 2016/0325058 A1 | 11/2016 | Samson et al. |
| 2016/0331917 A1* | 11/2016 | Bennett .................. A63B 23/18 |
| 2016/0339187 A1 | 11/2016 | Smaldone |
| 2016/0339190 A1 | 11/2016 | Morrison et al. |
| 2016/0354562 A1 | 12/2016 | Morrison |
| 2017/0020776 A1 | 1/2017 | Khasawneh et al. |
| 2017/0127945 A1 | 5/2017 | Reed |
| 2017/0173282 A1 | 6/2017 | O'Sullivan et al. |
| 2017/0296772 A1 | 10/2017 | Costella et al. |
| 2017/0333645 A1 | 11/2017 | Alizoti et al. |
| 2017/0333661 A1 | 11/2017 | Bennett et al. |
| 2018/0245999 A1* | 8/2018 | Erdler .................. G01L 9/0064 |

FOREIGN PATENT DOCUMENTS

| | | |
|---|---|---|
| EP | 0387222 B1 | 7/1993 |
| EP | 0824023 A1 | 2/1998 |
| EP | 0617628 B1 | 5/1998 |
| EP | 1338296 A1 | 8/2003 |
| EP | 1330283 B1 | 9/2006 |
| EP | 1993642 B1 | 1/2012 |
| EP | 1670533 B1 | 7/2012 |
| EP | 2300083 B1 | 5/2013 |
| EP | 2609954 A2 | 7/2013 |
| EP | 2376156 B1 | 1/2014 |
| EP | 2859906 A1 | 4/2015 |
| EP | 2563436 B1 | 10/2015 |
| EP | 2512566 B1 | 5/2016 |
| EP | 1613214 B1 | 10/2016 |
| EP | 3053620 A3 | 10/2016 |
| EP | 3097937 A1 | 11/2016 |
| GB | 2406283 A | 3/2005 |
| GB | 2479953 A | 2/2011 |
| GB | 2490770 A | 11/2012 |
| GB | 2512047 A | 9/2014 |
| GB | 2479953 B | 4/2015 |
| WO | WO9010470 A1 | 9/1990 |
| WO | WO9207599 A1 | 5/1992 |
| WO | WO9312823 A2 | 7/1993 |
| WO | WO9507723 A1 | 2/1995 |
| WO | WO9522365 A1 | 8/1995 |
| WO | WO9729799 A2 | 8/1997 |
| WO | WO9911310 A1 | 3/1999 |
| WO | WO0205879 A1 | 1/2002 |
| WO | WO0209574 A2 | 2/2002 |
| WO | WO02058771 A1 | 8/2002 |
| WO | WO03020349 A2 | 3/2003 |
| WO | WO03063937 A1 | 8/2003 |
| WO | WO03092576 A2 | 11/2003 |
| WO | WO03107523 A1 | 12/2003 |
| WO | WO2005042076 A1 | 5/2005 |
| WO | WO2005074455 A2 | 8/2005 |
| WO | WO2006123956 A1 | 11/2006 |
| WO | WO2007101438 A1 | 9/2007 |
| WO | WO2008112353 A2 | 9/2008 |
| WO | WO2009022139 A1 | 2/2009 |
| WO | WO2010023591 A2 | 3/2010 |
| WO | WO2010023591 A3 | 3/2010 |
| WO | WO2010110682 A1 | 9/2010 |
| WO | WO2010114392 A1 | 10/2010 |
| WO | WO2011003017 A1 | 1/2011 |
| WO | WO2011073806 A1 | 6/2011 |
| WO | WO2011083377 A1 | 7/2011 |
| WO | WO2011089486 A1 | 7/2011 |
| WO | WO2011089489 A1 | 7/2011 |
| WO | WO2011089490 A1 | 7/2011 |
| WO | WO2011130183 A2 | 10/2011 |
| WO | WO2011130583 A2 | 10/2011 |
| WO | WO2011135353 A1 | 11/2011 |
| WO | WO2012038861 A1 | 3/2012 |
| WO | WO2012064540 A2 | 5/2012 |
| WO | WO2012173992 A1 | 12/2012 |
| WO | WO2013028705 A2 | 2/2013 |
| WO | WO2013042002 A1 | 3/2013 |
| WO | WO2013043063 A1 | 3/2013 |
| WO | WO2013061240 A1 | 5/2013 |
| WO | WO2013061248 A1 | 5/2013 |
| WO | WO2013098334 A1 | 7/2013 |
| WO | WO2013124624 A1 | 8/2013 |
| WO | WO2014004437 A1 | 1/2014 |
| WO | WO2014033229 A1 | 3/2014 |
| WO | WO2014147550 A1 | 9/2014 |
| WO | WO2014202923 A1 | 12/2014 |
| WO | WO2014204511 A3 | 12/2014 |
| WO | WO2015002652 A1 | 1/2015 |
| WO | WO2015004554 A1 | 1/2015 |
| WO | WO2015004559 A2 | 1/2015 |
| WO | WO2015006701 A2 | 1/2015 |
| WO | WO2015008013 A1 | 1/2015 |
| WO | WO2015022595 A1 | 2/2015 |
| WO | WO2015030610 A2 | 3/2015 |
| WO | WO2015031472 A1 | 3/2015 |
| WO | WO2015036010 A1 | 3/2015 |
| WO | WO2015036010 A3 | 3/2015 |
| WO | WO2015036723 A1 | 3/2015 |
| WO | WO2015052519 A1 | 4/2015 |
| WO | WO2015104522 A1 | 7/2015 |
| WO | WO2015109259 A1 | 7/2015 |
| WO | WO2015114285 A1 | 8/2015 |
| WO | WO2015128173 A1 | 9/2015 |
| WO | WO2015133909 A1 | 9/2015 |
| WO | WO2015138454 A1 | 9/2015 |
| WO | WO2015144442 A1 | 10/2015 |
| WO | WO2015150029 A1 | 10/2015 |
| WO | WO2015154864 A2 | 10/2015 |
| WO | WO2015154865 A2 | 10/2015 |
| WO | WO2015174856 A1 | 11/2015 |
| WO | WO2015178907 A1 | 11/2015 |
| WO | WO2016025553 A1 | 2/2016 |
| WO | WO2016030521 A1 | 3/2016 |
| WO | WO2016033419 A1 | 3/2016 |
| WO | WO2016033421 A1 | 3/2016 |
| WO | WO2016043601 A1 | 3/2016 |
| WO | WO2016048435 A1 | 3/2016 |
| WO | WO2016049066 A1 | 3/2016 |
| WO | WO2016060863 A3 | 4/2016 |
| WO | WO 2016/079461 A1 | 5/2016 |
| WO | WO2016075525 A1 | 5/2016 |
| WO | WO2016081294 A1 | 5/2016 |
| WO | WO2016085988 A2 | 6/2016 |
| WO | WO2016090260 A1 | 6/2016 |
| WO | WO 2016/110804 A1 | 7/2016 |
| WO | WO2016111633 A1 | 7/2016 |
| WO | WO2016116591 A1 | 7/2016 |
| WO | WO2016162699 A1 | 10/2016 |
| WO | WO2016165029 A1 | 10/2016 |
| WO | WO2016181048 A1 | 11/2016 |
| WO | WO 2017/071879 A1 | 5/2017 |

(56) References Cited

FOREIGN PATENT DOCUMENTS

| | | |
|---|---|---|
| WO | WO 2017/178776 A1 | 10/2017 |
| WO | WO 2017/187116 A1 | 11/2017 |
| WO | WO 2017/194906 A1 | 11/2017 |

\* cited by examiner

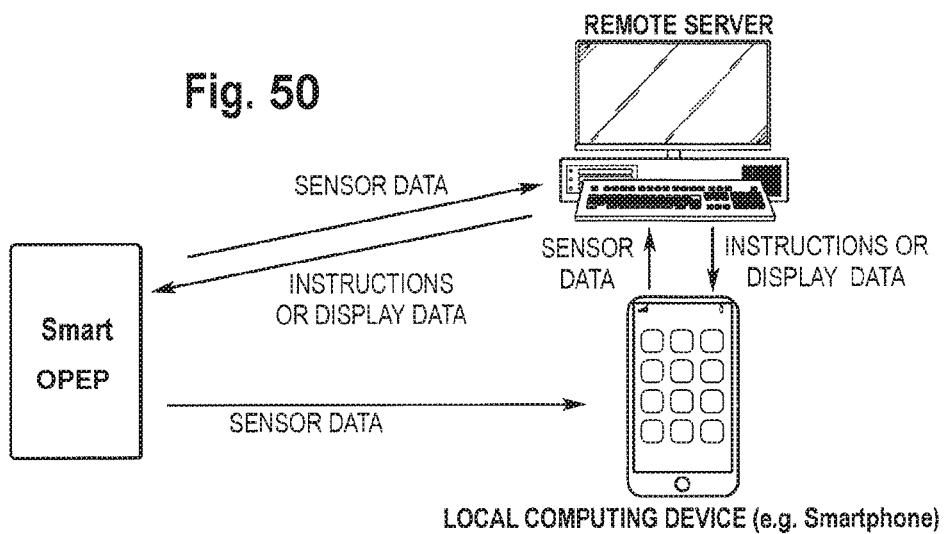

SMART OSCILLATING POSITIVE EXPIRATORY PRESSURE DEVICE

This application claims the benefit of U.S. Provisional Application No. 62/359,970, filed Jul. 8, 2016, the entire disclosure of which is hereby incorporated herein by reference.

TECHNICAL FIELD

The embodiments disclosed herein relate generally to a smart oscillating positive expiratory pressure device, and to methods for the use and assembly thereof.

BACKGROUND

Chronic obstructive pulmonary disease (COPD) and cystic fibrosis (CF) may cause an increase in the work of breathing that leads to dyspnea, respiratory muscle fatigue and general discomfort. Oscillating positive expiratory pressure (OPEP) treatments may be used as a drug-free way to clear excess mucus from the lungs of COPD and CF patients. OPEP may also be used post-operatively to reduce the risk of post-operative pulmonary complications. Typically, OPEP devices provide minimal feedback to the user or caregiver about the performance and/or effectiveness of the device during a treatment session. In addition, a large percentage (60%) of COPD patients do not adhere to prescribed therapy, with hospital systems carrying the burden of non-compliant patients that return to the hospital within 30 days. In addition, OPEP devices typically do not provide feedback regarding therapy adherence, progress tracking or proper usage technique.

SUMMARY

Briefly stated, in one embodiment, a smart OPEP device provides feedback to the user (patient or caregiver) regarding the frequency, mean pressure and amplitude of the pressure oscillations generated during a treatment session. In addition, data and information gathered regarding the performance of the OPEP device may be archived and analyzed to provide an overview of the user's progress, which may be made available to health care providers and insurers, for example, to monitor treatment adherence. Patient specific data may be provided to monitor trends over time. Performance targets and/or limits may be set to assist the user in achieving correct techniques, and treatment effectiveness may be evaluated by surveying the patient's quality of life and linking it to performance. In addition, with performance characteristics being measured, the user may set up the device, and the user may be motivated by various feedback including counting breaths or by playing games based on the measurements.

The present embodiments, together with further objects and advantages, will be best understood by reference to the following detailed description taken in conjunction with the accompanying drawings.

BRIEF DESCRIPTION OF THE DRAWINGS

FIG. 50 is a schematic illustration of a communication system.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components. It should be understood that the term "user" and "patient" as used herein refers to any user, including pediatric, adolescent or adult humans, and/or animals.

The term "smart" refers to features that follow the general format of having an input, where information is entered into the system, analysis, where the system acts on or modifies the information, and an output, wherein new information leaves the system. The phrase "performance characteristics" refers to measurements, such as frequency or amplitude, which quantify how well a device is functioning. Frequency is defined as the number of oscillations in one second, however, during a typical OPEP maneuver the rate of oscillations may not be consistent. Accordingly, frequency may be defined as the inverse of the time between oscillations (1/T), measured in Hz. This second definition calculates the frequency of each oscillation and is averaged over a period of time. Max pressure is the maximum pressure for each oscillation, typically measured in cmH$_2$O. Min pressure is the minimum pressure for each oscillation, typically measured in cmH$_2$O. Upper pressure is the average of the max pressures for a given time period, for example one second. Lower pressure is the average of min pressures for a given time period, for example one second. Amplitude is the difference between the upper and lower pressures. Mean pressure is the average of the upper and lower pressures. True mean pressure is the average of the entire pressure waveform for a given time period. The true mean pressure is typically lower than the means pressure because the typical pressure wave generated is not uniform, i.e., is skewed towards the min pressure.

Figure 1:
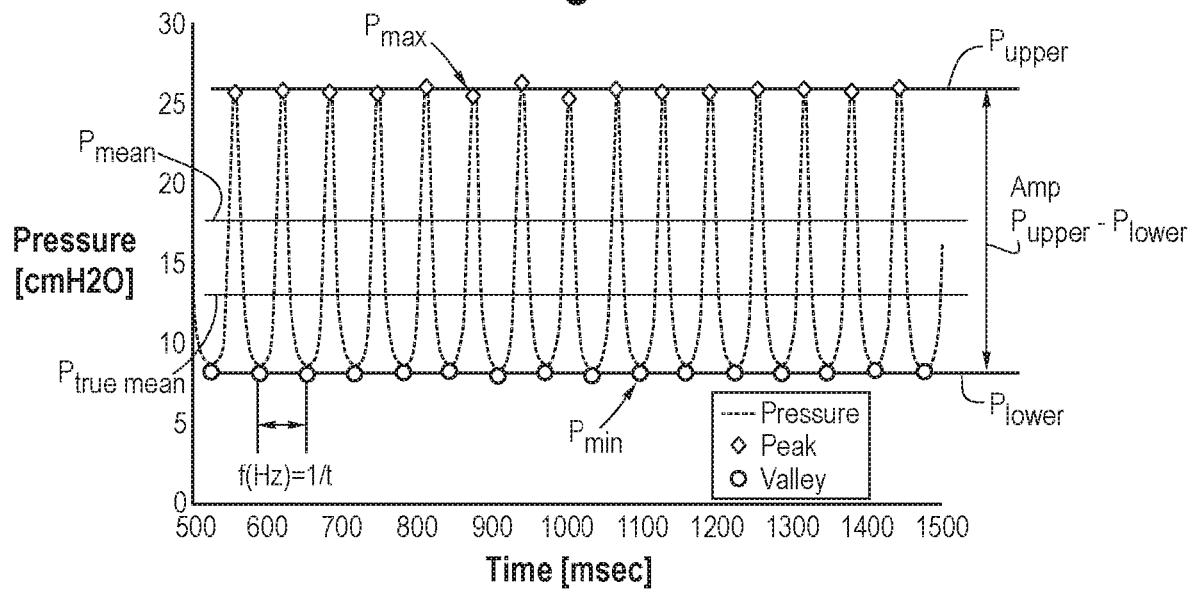
FIG. 1 is a graph of an OPEP pressure waveform that identifies various performance characteristics.
Figure 2:
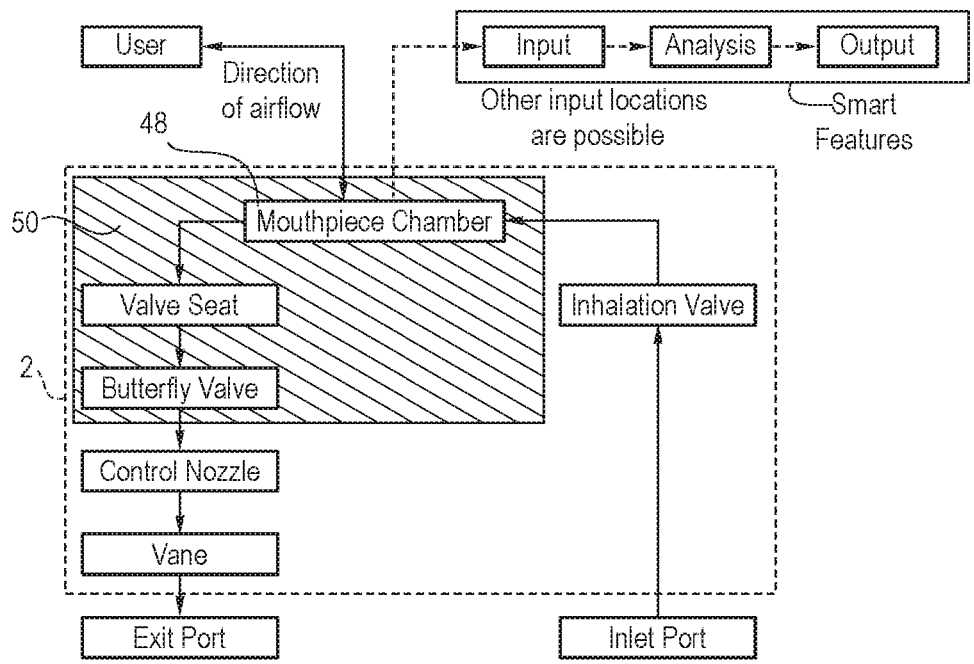
FIG. 2 is a block diagram of an OPEP device with smart capabilities.

Referring to FIG. 1, an OPEP pressure waveform is shown with various performance characteristics. FIG. 2 illustrates in block diagram form an OPEP device, illustrated as the dashed box that encloses the internal components, configured with smart capabilities. One exemplary OPEP device 2 is the Aerobika® OPEP device, shown in FIGS. 4, 24, 27-30, 47 and 48, available from Monaghan Medical Corporation, Plattsburg, N.Y. Various OPEP devices and structures are further disclosed in U.S. Pat. No. 8,985,111, issued Mar. 24, 2015 and entitled Oscillating Positive Expiratory Pressure Device, U.S. Pat. No. 8,539,951, issued Sep. 24, 2013 and entitled Oscillating Positive Expiratory Pressure Device, U.S. Pat. No. 9,220,855, issued Dec. 29, 2015 and entitled Oscillating Positive Expiratory Pressure Device, U.S. Pub. 2012/0304988, Published Dec. 6, 2012 and entitled Oscillating Positive Expiratory Pressure Device U.S. Pub. 2015/0297848, Published Oct. 22, 2015 and entitled Oscillating Positive Expiratory Pressure Device, and U.S. Pub. 2015/0053209, Published Feb. 26, 2015 and entitled Oscillating Positive Expiratory Pressure Device, the entire disclosures of which are hereby incorporated herein by reference. It should be understood that other OPEP devices may be configured with other components that create pressure oscillations.

A user, such as a patient, interacts with the OPEP device 2 via a mouthpiece 4. The OPEP device includes a housing 6 enclosing a mouthpiece chamber 48, a chamber 14, a chamber inlet 16 in communication with the mouthpiece, and one or more chamber outlets 18. Typically, OPEP devices permit the user to inhale and exhale, although some devices may permit exhalation only. The housing 6 has a front section 8, a rear section 10, and an inner casing 12, which may be separable so that the components contained therein can be periodically accessed, cleaned, or reconfigured, as required to maintain the ideal operating conditions.

Figure 47:
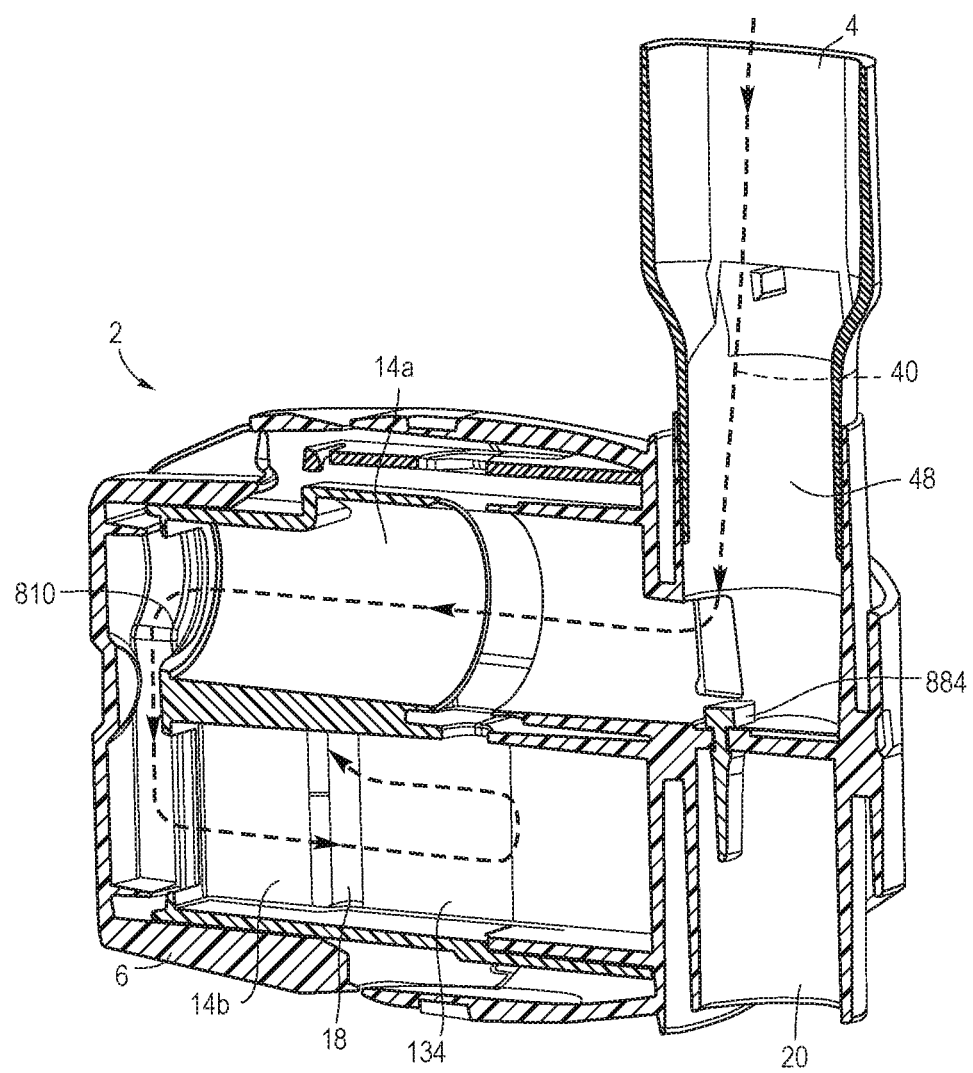
FIGS. 47 and 48 are cross-sectional views of an OPEP device shown with and without internal components respectively.
Figure 48:
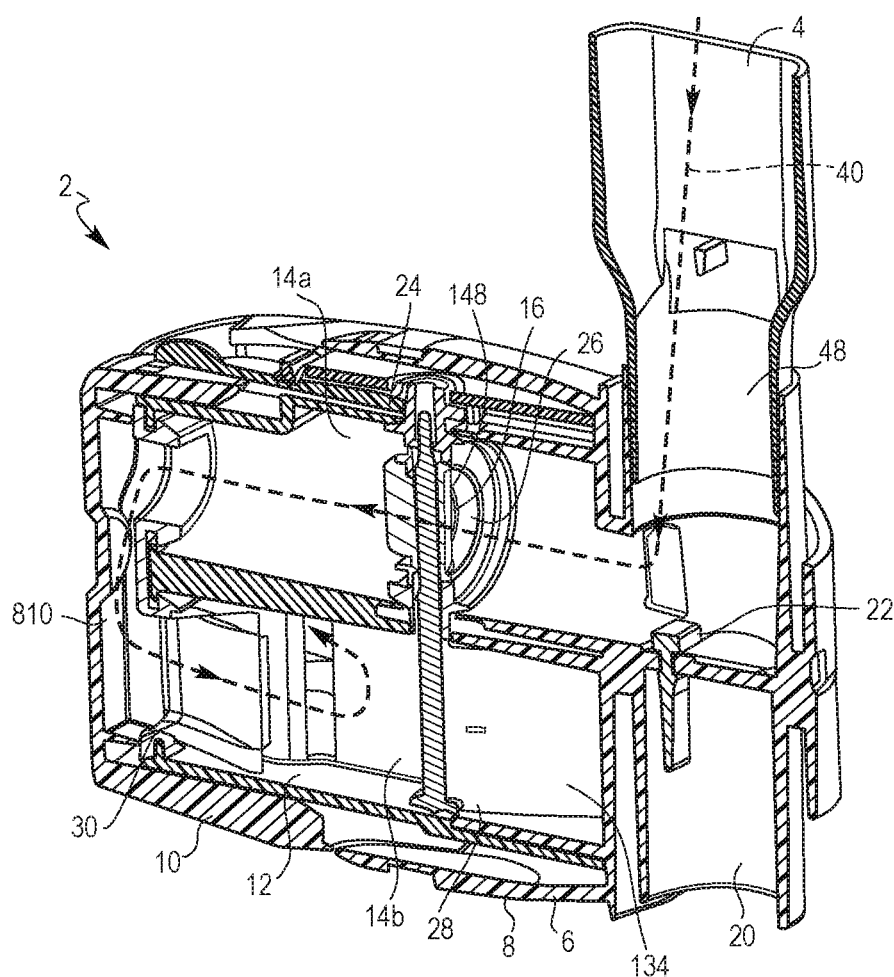

The OPEP device 2 also includes an inhalation port 20, a one-way valve 22, an adjustment mechanism 24, a restrictor member 26, a vane 28, and a variable nozzle 30, or vale assembly. As seen in FIGS. 47 and 48, the inner casing 12 is configured to fit within the housing 6 between the front section 8 and the rear section 10, and partially defines a chamber 14a, b, including a first chamber and a second chamber. First and second chamber outlets 18 are formed within the inner casing. The OPEP device 2 may include an adjustment mechanism 24 adapted to change the relative position of a chamber inlet 16. A user is able to conveniently adjust both the frequency and the amplitude of the OPEP therapy administered by the OPEP device 2 without opening the housing and disassembling the components of the OPEP device.

The OPEP device 2 may be adapted for use with other or additional interfaces, such as an aerosol delivery device. In this regard, the OPEP device 2 is equipped with an inhalation port 20 in fluid communication with the mouthpiece 4. As noted above, the inhalation port may include a separate one-way valve 22 configured to permit a user of the OPEP device 800 both to inhale the surrounding air through the one-way valve 22 and to exhale through the chamber inlet 16, without withdrawing the mouthpiece 4 of the OPEP device 2 from the user between periods of inhalation and exhalation. In addition, the aforementioned commercially available aerosol delivery devices may be connected to the inhalation port 20 for the simultaneous administration of aerosol therapy (upon inhalation) and OPEP therapy (upon exhalation).

The exhalation flow path 40 begins at the mouthpiece 4 and is directed through the mouthpiece chamber 48 toward the chamber inlet 16, which in operation may or may not be blocked by the restrictor member 26, or valve assembly which may include a valve seat and butterfly valve. After passing through the chamber inlet 16, the exhalation flow path 40 enters the first chamber 14 and makes a 180° turn toward the variable nozzle 30. After passing through an orifice of the variable nozzle, the exhalation flow path enters the second chamber 14. In the second chamber 14, the exhalation flow path 40 may exit the second chamber 41, and ultimately the housing 6, through at least one of the chamber outlets 18. It should be understood that the exhalation flow path 40 identified by the dashed line is exemplary, and that air exhaled into the OPEP device 2 may flow in any number of directions or paths as it traverses from the mouthpiece 4 to the outlets 18.

The shaded area 50 in FIG. 2 represents the internal volume, defined for example by the mouthpiece chamber 48, which becomes pressurized when the valve mechanism closes. The shaded area outside of the OPEP device boundary represents the "smart" features that include three operations: input, analysis and output. The input may come from the high pressure zone 50 as shown in FIG. 2, although it may originate from another part of the device depending on the measurement being taken or registered.

Inputs

Figure 3:
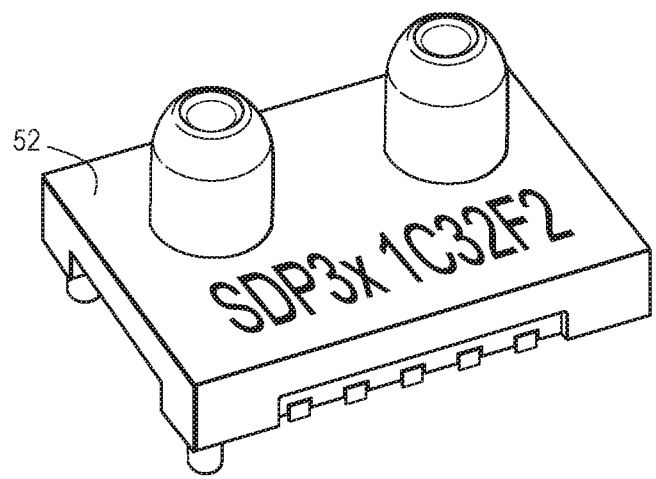
FIG. 3 is a perspective view of a pressure sensor.
Figure 4:
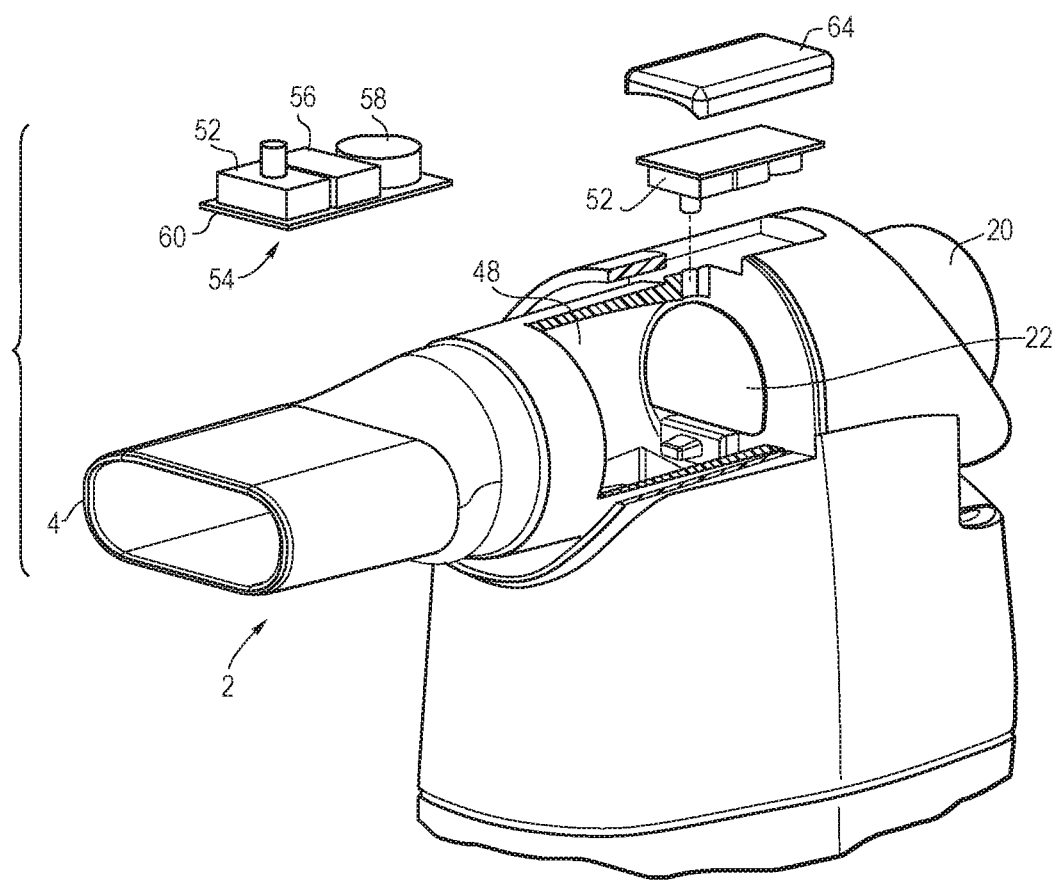
FIG. 4 is a partial, exploded perspective view of one embodiment of a smart OPEP.

The term "input" refers to any information that enters the smart OPEP system, and may take the form of raw data from a sensor, a command to start a process or personal data entered by the user. For example, the input may be a signal from one or more input components, such as a sensor. For example, as shown in FIGS. 3 and 4, a pressure sensor 52 generates an electrical signal as a function of the pressure in the system, or chamber 48. The pressure sensor may be used to calculate any of the performance characteristics referred to above, as well as to evaluate the user's technique. A sensor assembly 54 may include a housing 202 for a pressure sensor 52 placed on a printed circuit board (PCB), along with a BTLE module 56, a processor (e.g., microprocessor) 60, LED indicator 154, memory, wireless communication capabilities and a battery 58, and may communicate with an output component, for example a user's (patient, caregiver and/or other authorized user) computing device, such as a mobile device 62, including a smart phone or tablet computer. The assembly may be configured as a removable control module. A single pressure sensor 52 may provide all of the measurement requirements. The pressure sensor may be a differential, absolute or gauge type of sensor. The sensor assembly is coupled to the OPEP device, with a cover 64 disposed over the assembly. The input component is in considered to be in "communication" with the chamber 48 if it is able to sense or measure the pressure or flow therein, even if the input component is separated from the interior of the chamber, for example by a membrane or other substrate. The input component is operative to sense a flow and/or pressure and generate an input signal correlated to the flow or pressure.

Figure 5A:
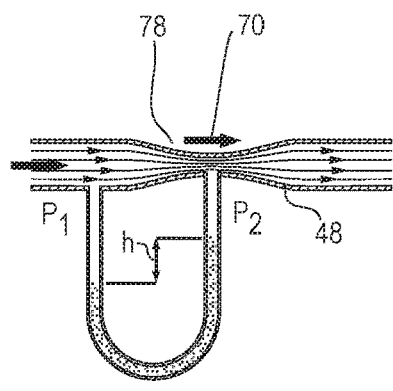
FIGS. 5A-G show various flow sensors.
Figure 5B:
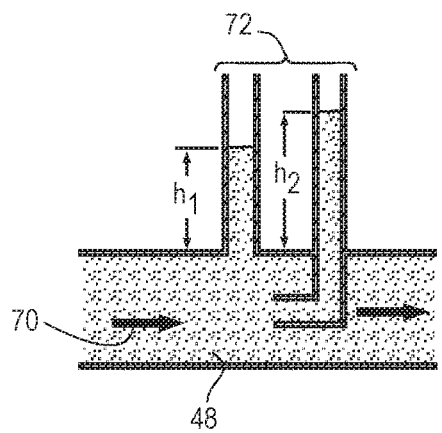
Figure 5C:
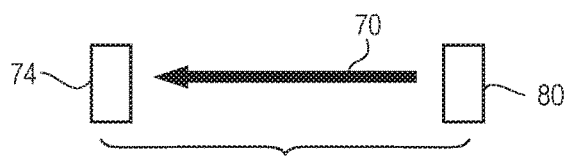
Figure 5D:
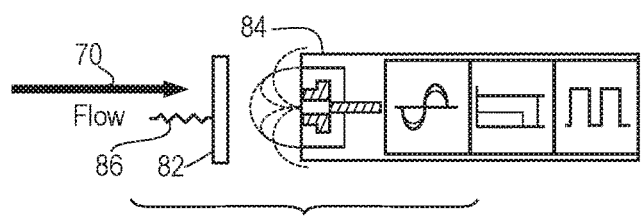
Figure 5E:
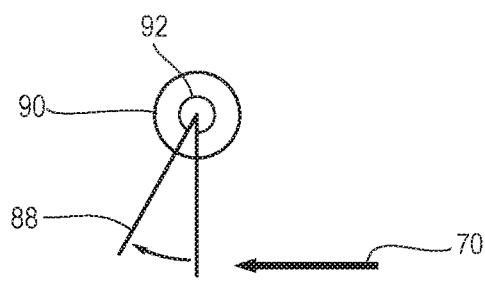
Figure 5F:
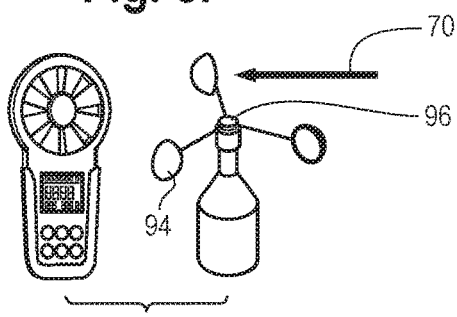
Figure 5G:
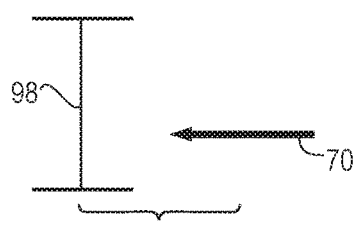

Referring to FIGS. 5A-G, various flow sensors are shown that generate an electrical signal as a function of the airflow 70 in the system. A flow sensor may be used to calculate the frequency, as well as evaluate the user's technique. The flow sensors may include incorporating a venturi 78 into the shape of the mouthpiece chamber (FIG. 5A), incorporating pitot tubes 72, which compare pressure generated by flow stagnation at the entrance of the pitot tube to that of the surrounding fluid and determine the fluid velocity (FIG. 5B), or using sound transmitters/receivers 74 to measure the time it takes sound to travel from transmitter 1 (74) to receiver 2 (80), and then from transmitter 2 (80) to receiver 1 (74) (FIG. 5C) and calculating the flow based on the different in time being proportional to the flow velocity. Alternatively, as shown in FIG. 5D, air flow causes displacement in a magnetic component 82, which in turn changes the inductance of a coil 84. The inductance of the coil is related to displacement, which may be correlated to flow rate. A biasing spring 86 (e.g., tension or compression), may be provided to return the magnet to the "zero-flow" position when no flow is present. Referring to FIG. 5E, air flow cause a vane 88 to move that changes the resistance of a potentiometer 90, which is related to flow rate. Again, a biasing spring 92 (e.g., torsion) may be include to return the vane to the "zero-flow" position when no flow is present. Referring to FIG. 5F, a vane 94, having for example a plurality of blades, rotates in response to a flow, with the speed of the rotation shaft 96 correlated to the proportional flow rate. Referring to FIG. 5G, flow 70 passes over a heater wire 98, which then begins to cool. More current is passed through the wire to maintain a constant temperature, with the amount of measured current correlated to the flow rate.

Figure 43A:
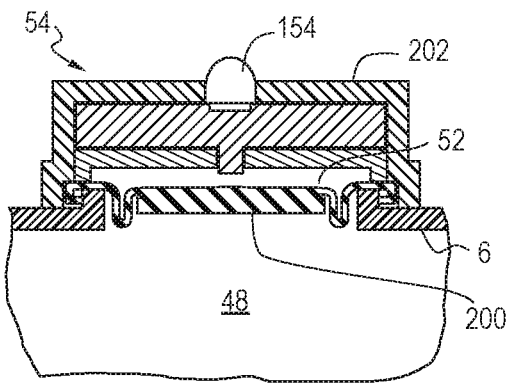
FIGS. 43A and B are partial cross-sectional views of control module in an installed and uninstalled position.
Figure 43B:
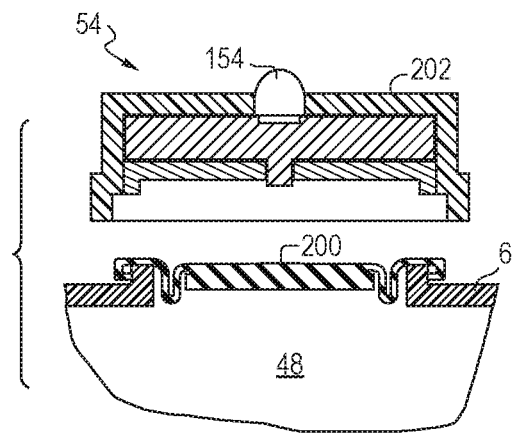

Referring to FIGS. 43A and B, the control module 54 is not in fluid communication with the internal volume, e.g., mouthpiece chamber 48, or the OPEP device, but rather is separated by flexible membrane 200, which moves in response to changes in pressure within the device, for example the chamber 48. In this way, the OPEP device, or housing, may be cleaned without damaging the electronic components, and those components also are not in fluid communication with the user's inspiratory and/or expiratory breath or flow. When the control module is removed, or moved to an uninstalled position, the flexible membrane 200 remains attached to the housing 6.

At rest, the pressure in the OPEP chamber 48, 14a, 14b, is atmospheric or ambient. As pressure in the chamber increases, an upward/outward force is applied to the membrane 200, causing it to move towards the module 54. Since a measurement chamber 202, formed between the membrane 200 and the module, is sealed with the membrane, the volume of air in the measurement chamber 202 is decreased with while the pressure in the chamber 202 is increased. The control module measures the pressure change inside the sealed measurement chamber and determines the pressure inside the OPEP chamber 48 (or 14a, 14b) using a conversion algorithm. During inhalation, the pressure in the chamber 48, 14a and/or 14b, becomes negative, which imparts a downward or inward force on the membrane 202. As the flexible membrane is pulled away from the control module 54, the pressure inside the measurement chamber is decreased, or becomes negative. Again, the control module 54 measures this pressure chamber and determines the corresponding, or actual, pressure in the chamber 48. As such, the module 54 measures pressure without being in fluid communication with the chamber 48 and the user's inspiratory/expiratory flow.

Figure 44:
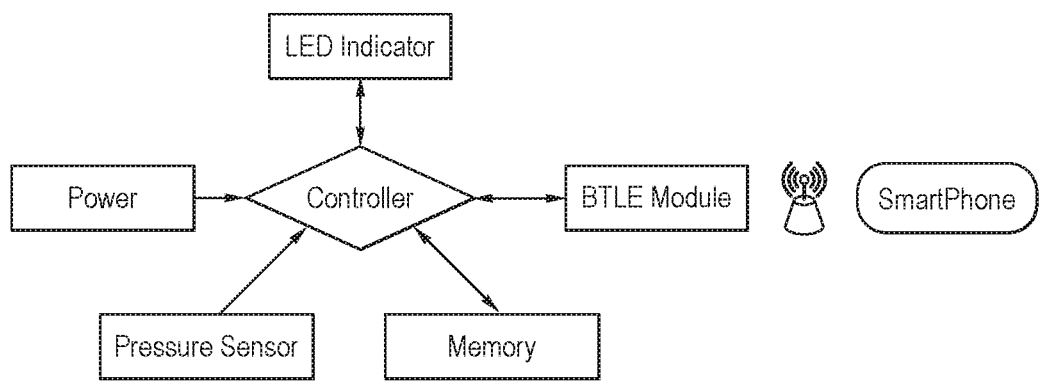
FIG. 44 is a block diagram of a smart OPEP system.

Referring to FIG. 44, the controller, BTLE module, LED indicator, memory sensor are in electrical contact with the power source, e.g., battery. The controller receives a signal from the pressure sensor and sends/receives data to/from the BTLE module, which then communicate with the mobile device 62, or other user interface and/or processor. The controller also sends a signal to the LED indicator 154 as required, and can save data to, and recall data from, the internal memory.

Figure 6:
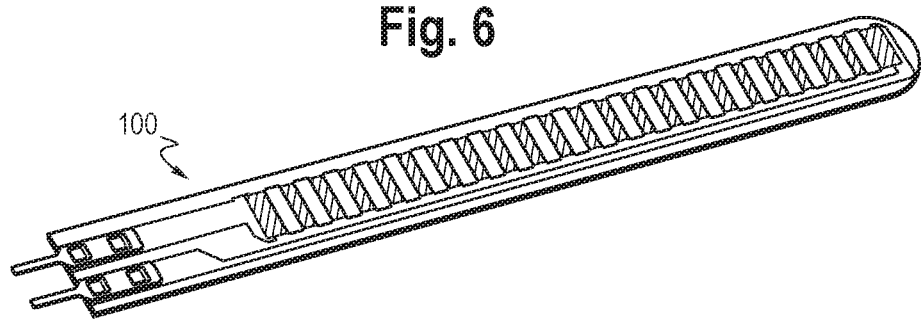
FIG. 6 is a perspective view of a flex sensor.
Figure 7A:
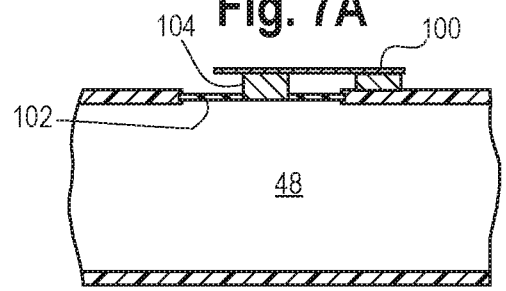
FIGS. 7A and B are partial cross-sectional views of an OPEP device with a flex sensor in an un-flexed and flexed configuration respectively.
Figure 7B:
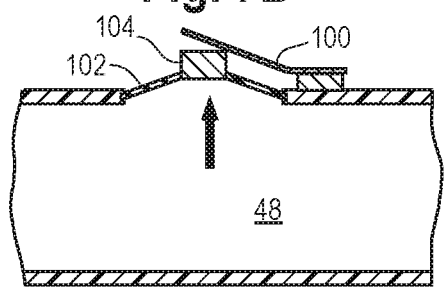

Referring to FIGS. 6, 7A and B, a flex sensor 100 is shown as being disposed adjacent a high pressure cavity or zone defined by the chamber 48. The resistance through the flex sensor is proportional to the amount of flex applied and may be used as an indirect measurement of pressure. The flex sensor may be positioned on the low pressure side of a silicone membrane 102. The membrane 102 moves in response to a pressure increase inside the cavity or system, causing the sensor 100, cantilevered over the membrane or an actuation pad extending therefrom, to flex. The membrane 102 may include an actuation pad 104 that engages the flex sensor 100. The resistance change from the flexing maybe correlated to the pressure in the system. The electronic components, including the sensor, are separated from the flow path by the membrane 102, which prevents contamination. Cleanliness of the flow path may be particularly important to CF patients. At the same time, the electronic components may be easily removed for cleaning and disinfecting.

Figure 8A:
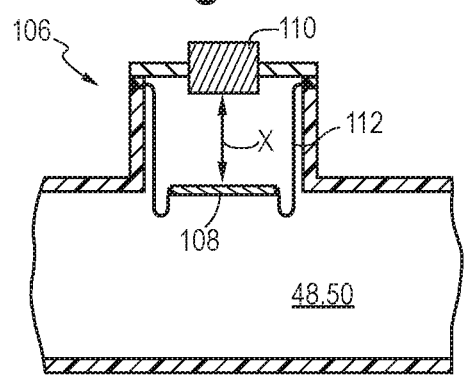
FIGS. 8A and B are partial cross-sectional views of an OPEP device with a non-contact position sensor in first and second pressure configurations respectively.
Figure 8B:
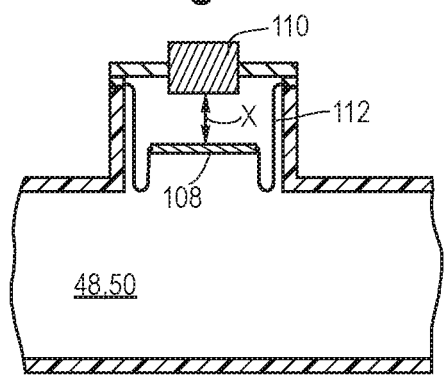

Referring to FIGS. 8A and B, a non-contact position sensor 106 may provide either an absolute or relative position of an object, and like the flex sensor, may be used to indirectly measures pressure changes. Some types of non-contact position sensors are capacitive displacement sensor, ultrasonic sensors, and proximity sensors. The sensors may be used to measure the displacement of a moveable surface that respond to pressure changes. At ambient, or atmospheric pressure, a base component 108 coupled to a silicone bellow 112 is positioned a distance "x" mm from a sensor 110. The base 108, which is planar, has a thickness greater than the thickness of the bellow 112. As the pressure increases, the base 108, attached for example with rolling bellows, is moved toward the sensor 110, e.g., cap active displacement sensor, and the distance "x" decreases. Therefore, the distance between the base 108 and the sensor 110 is inversely proportional to the pressure. If the pressure increases, the distance decrease, and vice versa. The sensor may also measure negative pressure, for examples as the distance "x" increases.

Figure 9:
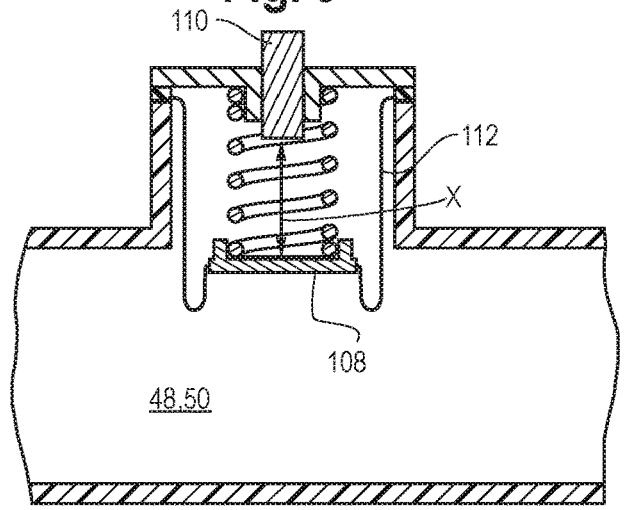
FIG. 9 is a partial cross-sectional view of an OPEP device with a spring assisted non-contact position sensor.

If the pressure inside the device is too high, the silicone bellows may not be stiff enough to resist bottoming out. As shown in FIG. 9, an assist spring 112, such as a mechanical compression spring, may be disposed between the base 108 and sensor 110. In this way, the system is able to measure increased pressures. As with the embodiment of FIGS. 7A and B, the electronic components of FIGS. 8A, B and 9 are separated and isolated from the flow path by the silicone membrane or bellows. In addition, the electronic components may be removable.

Figure 10:
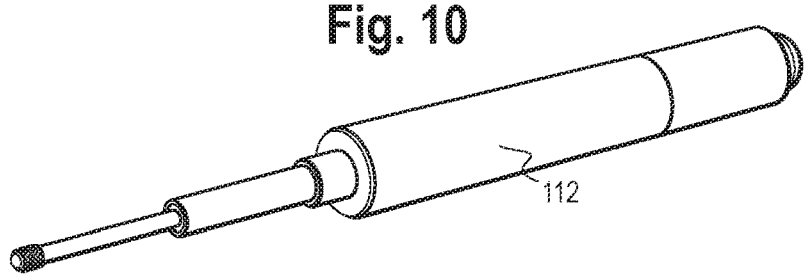
FIG. 10 is a perspective view of a linear variable differential transformer (LVDT).

Referring to FIG. 10, a linear variable differential transformer (LVDT) 112 is shown. The LVDT is a contact sensor, and directly measures the linear displacement of the flexible membrane 102 or base 108 shown in the prior embodiments. The displacement may be correlated to pressure.

Figure 11:
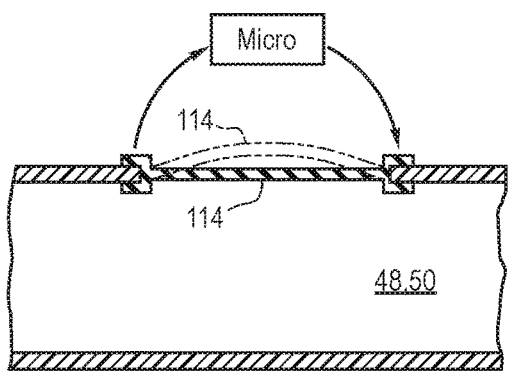
FIG. 11 is a partial cross-sectional view of an OPEP device with a conductive membrane.

Referring to FIG. 11, a conductive membrane 114 is provided. The membrane is made using silicone with conductive properties. As the pressure inside of the system increases, the membrane deflects and the resistance or capacitance changes, which may be correlated to the pressure.

Figure 12:
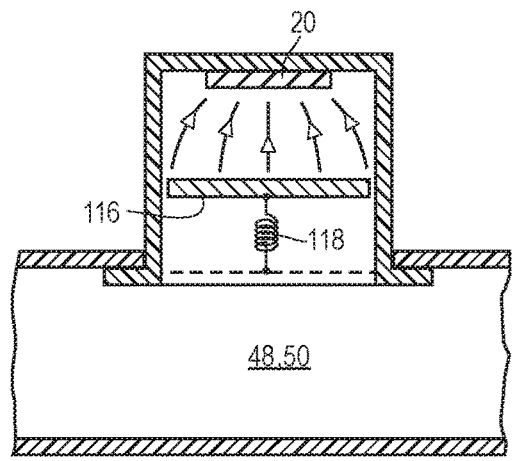
FIG. 12 is a partial cross-sectional view of an OPEP device with a Hall Effect sensor.

Referring to FIG. 12, a magnet 116 is configured with a spring. As the pressure inside the system changes, the distance between the magnet and Hall Effect sensor 120 may be correlated to pressure. A return spring 118 may be coupled to the magnet.

Figure 13:
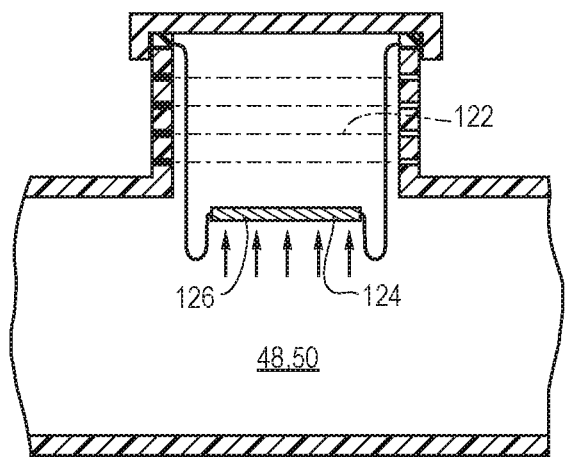
FIG. 13 is a partial cross-sectional view of an OPEP device with a light curtain sensor.

Referring to FIG. 13, a light curtain 122 may be used to determine the displacement of a membrane 124, which is displaced by pressure. As the pressure increases, a base or platform portion 126 of a membrane moves through the light curtain 122, with the movement correlated to pressure.

Figure 14:
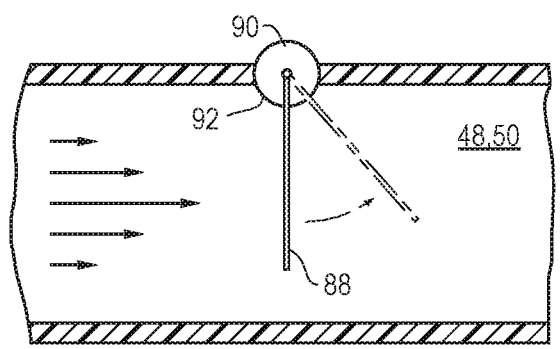
FIG. 14 is a partial cross-sectional view of an OPEP device with a potentiometer vane.

Referring to FIGS. 5E and 14, a potentiometer vane 88 is disposed in the flow path 70. The amount of rotation of the vane is proportional to the flow inside the chamber, and ultimately to pressure. A return spring 92 is incorporated to reset the vane when zero flow is present.

Figure 15:
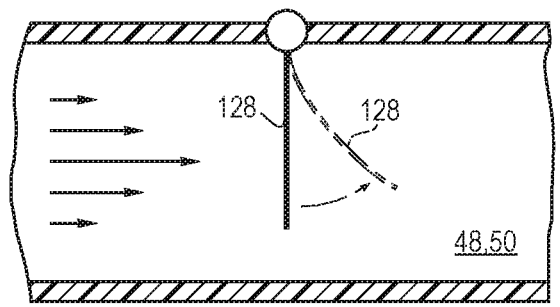
FIG. 15 is a partial cross-sectional view of an OPEP device with a piezo flex sensor.

Referring to FIG. 15, a Piezo flex sensor 128 is disposed in the flow path. The flex sensor bends in response to the air flow of the chamber. As the sensor bends, the resistance changes. The change of resistance may be correlated to flow rate, and pressure.

Figure 16:
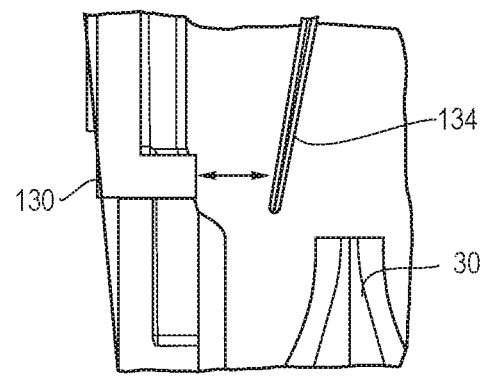
FIG. 16 is a partial cross-sectional view of an OPEP device with a proximity sensor with a vane in a closed position.
Figure 17:
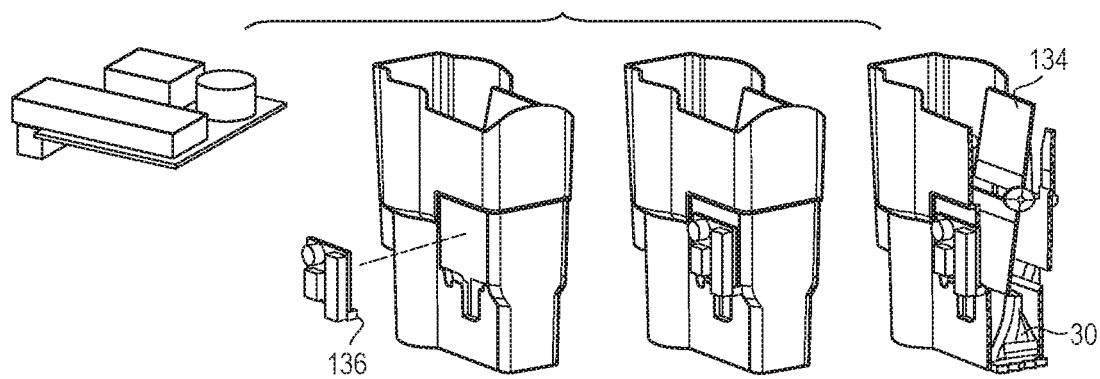
FIG. 17 is a series of exploded perspective views of an OPEP device with a proximity sensor.

Referring to FIGS. 16 and 17, a proximity sensor 130 is used to detect the presence of nearby objects without physical contact. In this case, a proximity sensor 130 is used to detect if the tip of a vane 134 is present. Every time the vane oscillates, the sensor would detect its position and the time between oscillations can be calculated. In the closed position, the vane comes within 5 mm of the sensor at the highest resistance setting. A lower resistance setting will decrease the distance between the vane and the sensor.

Another embodiment uses a proximity sensor 136 to monitor the control nozzle 30. As the valve/vane mechanism 134 opens and closes to create the pressure oscillations, the flow within the device also oscillates. When the flow is high the control nozzle 30 is in the open state, and when the flow is low the control nozzle is in the closed state. The open/closed motion of the control nozzle may be detected and converted to frequency.

An accelerometer measures proper acceleration and can be used to calculate frequency from the vibrations as the valve/vane mechanism 26, 134 opens and closes. The accelerometer may be placed on the device in the location that provides the greatest vibration.

Figure 18:
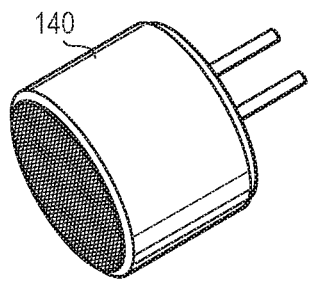
FIG. 18 is a perspective view of a PCB microphone.
Figure 19:
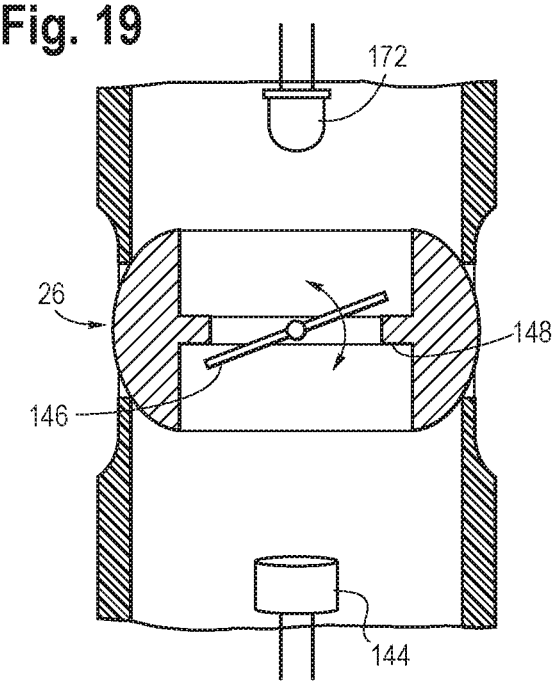
FIG. 19 is a partial cross-sectional view of an OPEP device with a LED/Photo sensor.

A microphone 140, similar to the one shown in FIG. 18, may be mounted on a PCB and placed in the same location as the proximity sensor in FIGS. 16 and/or 17. The microphone would pick up the sound of the airflow starting and stopping, plus any mechanical contact that occurs with the oscillating mechanism.

An LED 142 and Photo sensor 144 may be used to calculate the frequency of the oscillating mechanism. In this arrangement, the LED is located on one side of the butterfly valve 146 and the photo sensor is on the other. As the valve opens, light passes through the valve seat and is measured by the photo sensor. As the valve closes, or engages the seat 148, light is blocked from reaching the photo sensor. The timing of this data can be used to calculate the frequency.

Figure 20:
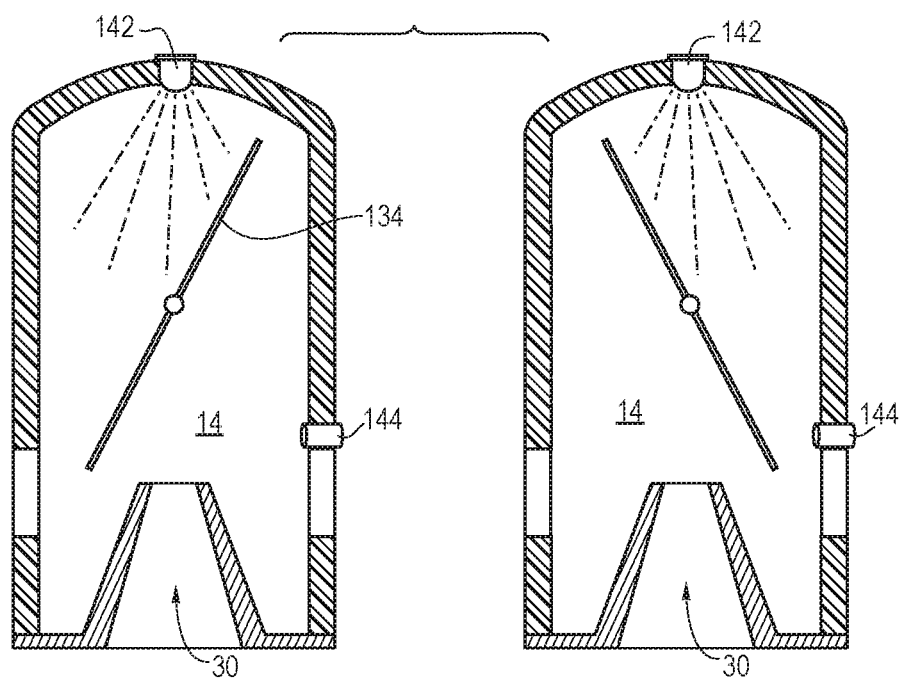
FIG. 20 is a partial cross-sectional view of an OPEP device with another embodiment of a LED/Photo sensor.

Another LED/Photo sensor arrangement is shown in FIG. 20. In this arrangement, the LED is located at the far side of the vane chamber 14b, and the photo sensor is located on the side wall by one of the exhaust ports 18. As the vane 134 pivots to one side, it blocks light from reaching the photo sensor. As the vane pivots to the other side, light from the LED is able to reach the photo sensor. The timing of this data may be used to calculate the frequency.

Figure 21:
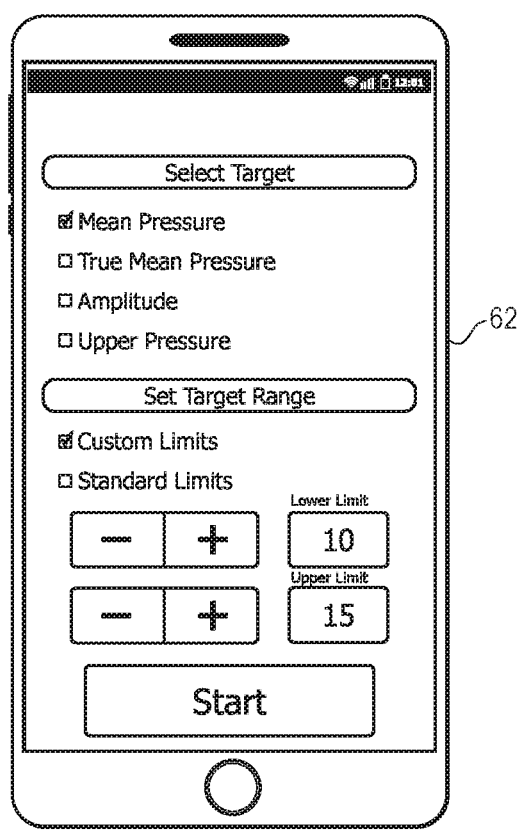
FIG. 21 is a view of a user interface with an input screen.

Referring to FIG. 21, a mobile device 62, such as a smartphone, may include an app providing an INPUT if the Smart features are not integrated into the OPEP device. The app may allow selection of the desired feedback and adjustment of targets and/or limits.

Figure 22:
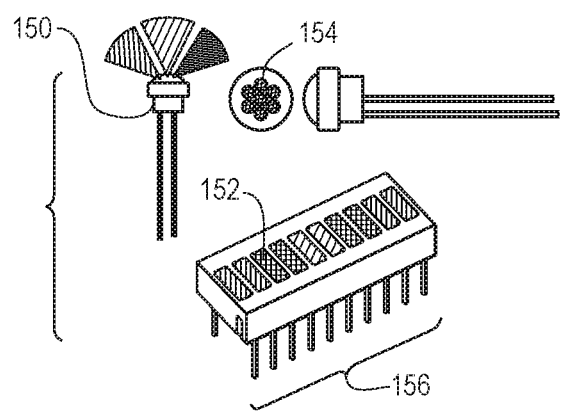
FIG. 22 shows various LED outputs.

Input on the user's quality of life is used to calculate a QoL score which may be correlated with DFP performance. Various inputs may be used to calculate a QoL score and algorithms could be tailored or adjusted for different disease types. User input may be performed with an auxiliary input component, such as computer device, for example a smartphone app. Some examples of QoL inputs are:

St. George's Respiratory questionnaire for COPD
Simplified questionnaire
User's journal
Steps/day
Number of hours the user is sedentary Outputs Referring to FIGS. 22 and 23, an output is defined as new information that is leaving the Smart OPEP 'system', with the information being communicated by an output component. The output may take the form of visual, audible, and sensory feedback, or be related to the user's quality of life and disease progress. A number of outputs and output components are suitable, including a visual output component, which may be easily integrated into the Smart OPEP device and allow several levels of feedback. For example, an array 150 of three (3) LEDs 152, each with a different colour may indicate if the input is low, high, or acceptable. Instead of three (3) separate LEDs, a single tri-colour LED 154 may also be used. If more than three (3) discreet states of feedback are required, then a LED bar graph 156 may be used.

Audible and sensory/tactile (vibration) outputs and output components may also be used to provide feedback to the user. For example, sound or vibration occurs while the input is within the acceptable range, or if the input exceeds a specified limit.

A mobile device 62, or other computer interface, may function as the output component and provide an interface with a smartphone app as an output if the Smart features are not integrated into the OPEP device. The app could display real-time performance characteristics, data trends, or games that motivate the user to complete a session.

Feature: Performance Targets

This feature provides feedback to the user based on specific performance targets. For example, if the mean pressure is to be within 10 to 15 cmH2O, this feature would notify the user that their mean pressure is too high, too low, or acceptable. The performance targets can be set by the patient or health care provider, or default to limits based on generally accepted treatment protocols.

Figure 24:
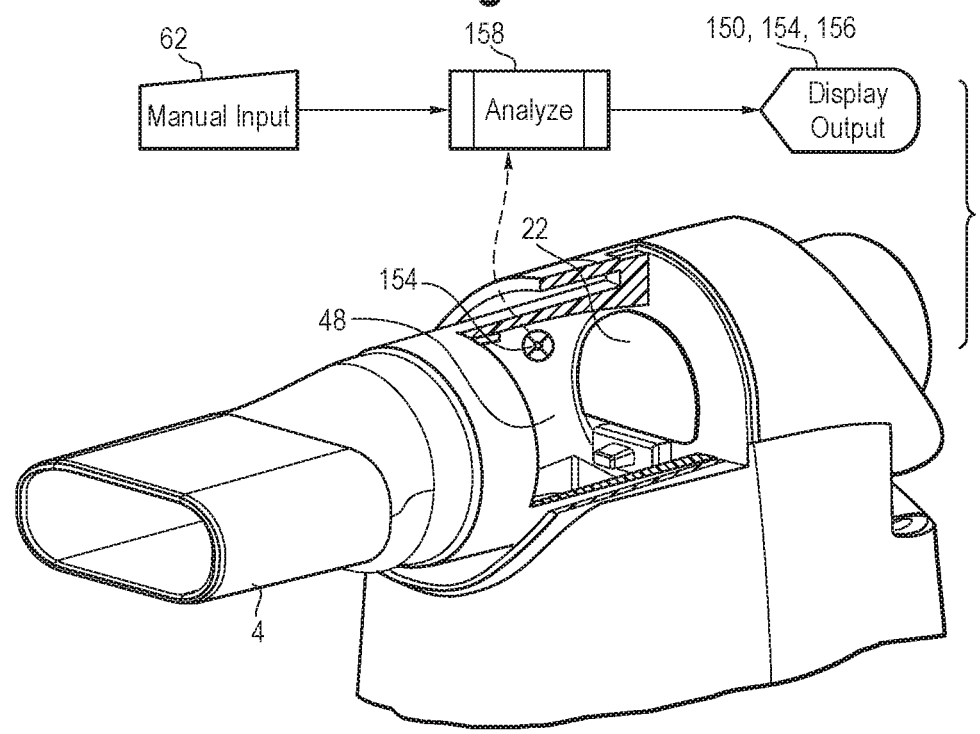
FIG. 24 is a partial view of a layout for a smart OPEP device.

The general layout for this feature is shown below in FIG. 24 and includes a sensor 154, which may include without limitation any one of the sensors previously disclosed herein, or combinations thereof, the ability to process raw data, including for example a processor 158, an output component 150, 154, 156 to display feedback, and if necessary, the ability to enter performance limits manually. The location of the sensor may change depending on the type of sensor selected or the performance characteristic being measured as disclosed herein with respect to various embodiments.

The performance characteristics that could be included in this feature are referred to above and herein. The following table lists exemplary performance characteristics and various suitable sensors for measuring the characteristics.

TABLE 1

Performance Characteristics

| Performance Characteristic | Frequency | Mean Pressure | True Mean Pressure | Amplitude | Upper Pressure | Lower Pressure |
|---|---|---|---|---|---|---|
| Pressure Sensor | X | X | X | X | X | X |
| Flex Sensor | X | X | X | X | X | X |
| Non-contact Position Sensor | X | X | X | X | X | X |
| LVDT | X | X | X | X | X | X |
| Conductive Membrane | X | X | X | X | X | X |
| Hall Effect Sensor | X | X | X | X | X | X |
| Light Curtain | X | X | X | X | X | X |
| Flow Sensor | X | | | | | |
| Potentiometer Vane | X | | | | | |
| Piezo Flex Sensor | X | | | | | |
| LED/Photo Sensor | X | | | | | |
| Proximity Sensor | X | | | | | |
| Accelerometer | X | | | | | |
| Microphone | X | | | | | |

Figure 25:
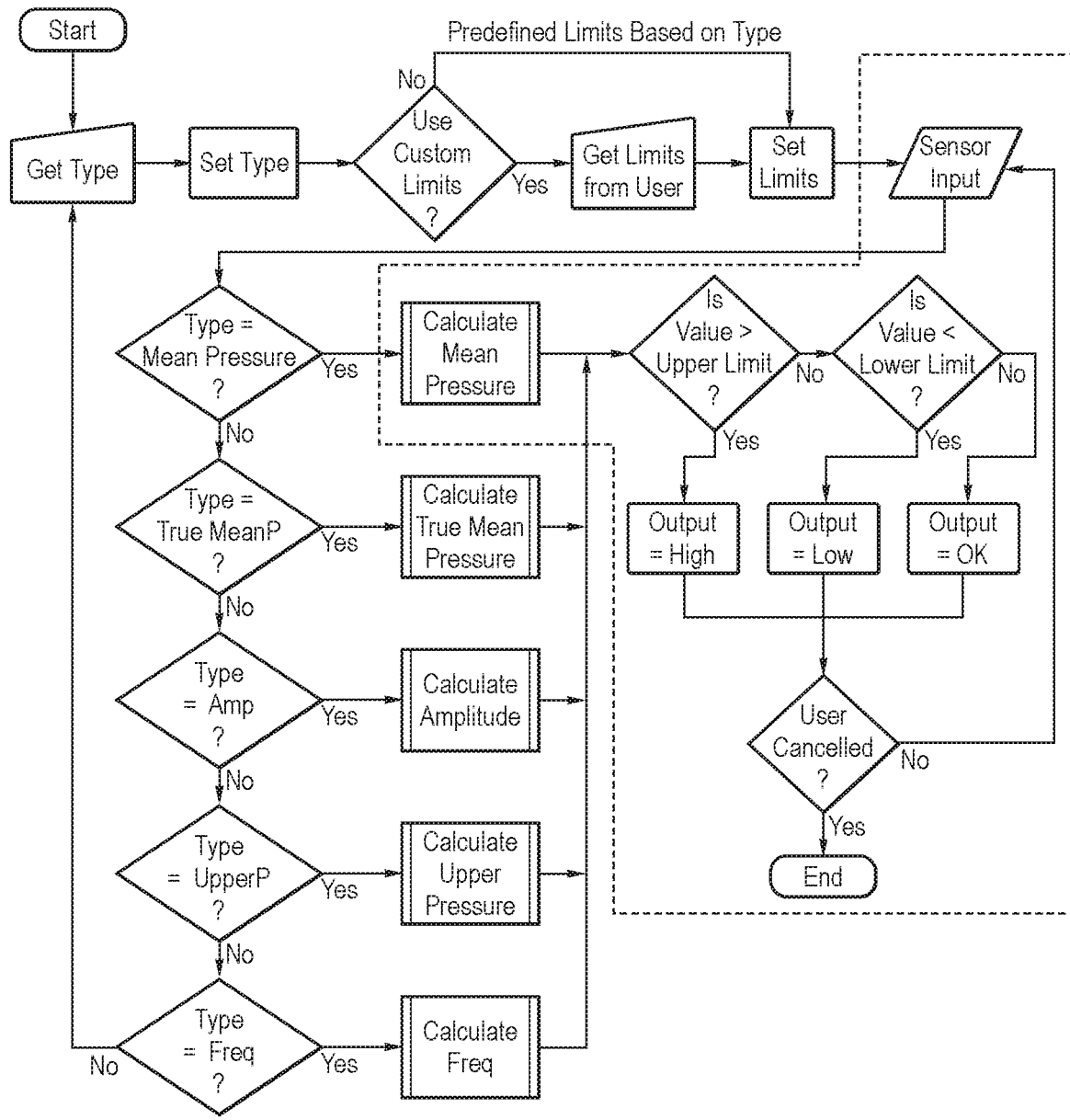
FIG. 25 is a flow chart for performance targets for an OPEP device.

The flow chart for this feature is shown in FIG. 25. The dashed area represents an integrated embodiment that does not allow the target limits to be adjusted and in this case provides feedback on the mean pressure.

In operation, the user first selects the type of feedback. The "Get Type & Set Type" define the performance characteristic to be analyzed. Next, the user decides if custom targets are to be used and enters the limits. If not, default limits are set based on the performance characteristic selected. Next, the sensor 154 begins sending raw data and the selected performance characteristic is calculated. Next, a series of decisions are made based on the calculated value of the performance characteristic. If the value is greater than the upper limit, then the output is high. If the value is less than the lower limit, then the output is low. If the value is neither, than the output is OK. Next, the flow chart checks if the user has selected to end the feedback. If not, then the cycle repeats. The above logic provides 3 discreet states of feedback. If required, additional logic could be added to provide a finer resolution to the feedback.

The analysis may either be completed using a processor 158, e.g., a microcontroller, embedded in the PCB, or may be performed using an external computing device, such as mobile device, including a smartphone or tablet. As seen in Table 1, frequency may be determined from any sensor, however, pressure outputs require a pressure sensor (either direct or indirect). In order to calculate frequency from a pressure input, processing techniques such as: Peak-to-Peak time, Fourier analysis, or Auto-correlation may be used. FIG. 1 illustrates an example of a pressure waveform that has been processed using a Peak-to-Peak technique.

Figure 26:
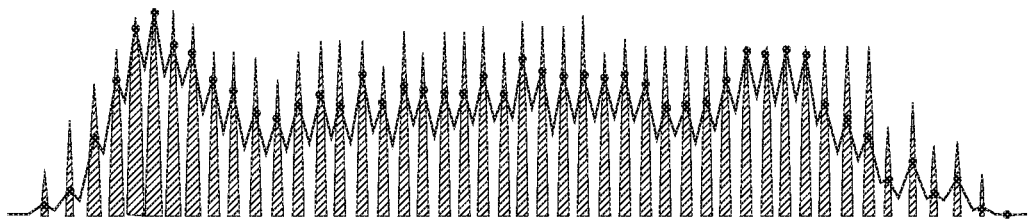
FIG. 26 is an exemplary graph of a sound signal.

If the input is a sound signal it can be averaged to simplify the waveform. The simpler waveform may then be processed in the same way as a pressure signal to determine frequency. Referring to FIG. 26, the raw sound data (bars) has been averaged using the Root Sum of Squares technique and the result is shown by the line. Each peak (dot) is then identified and the time between peaks is calculated and used to determine the frequency.

The output for this feature can be visual 160, audible 162, or sensory 164, and can be integrated into the device. An example of an integrated solution is shown in FIGS. 4, and 27-29. In one embodiment, an integrated solution would not provide for the selection of the performance characteristics or adjustment of the performance limits. In other embodiments, the integrated solution may provide a user interface permitting such selection and adjustment, for example through a keypad, buttons or touchscreen.

Figure 31:
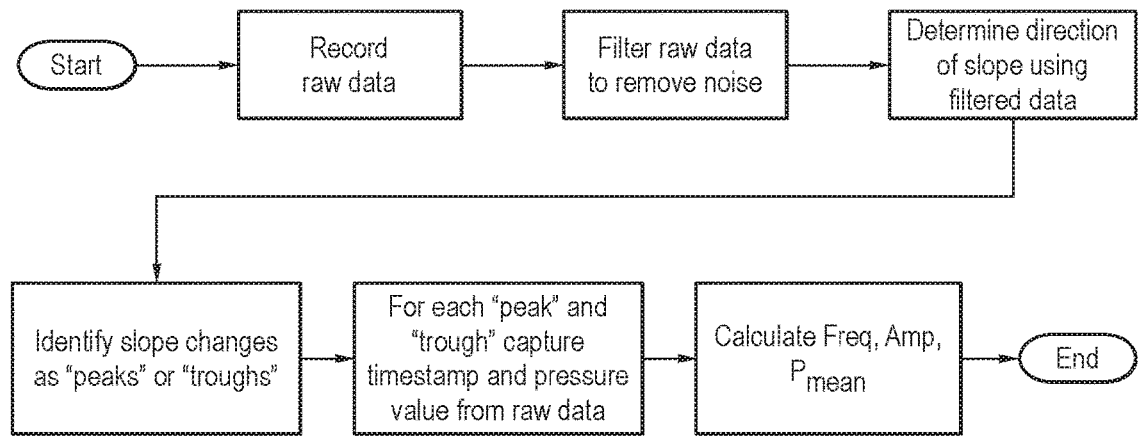
FIG. 31 is a flow chart for a smart OPEP algorithm.
Figure 46A:
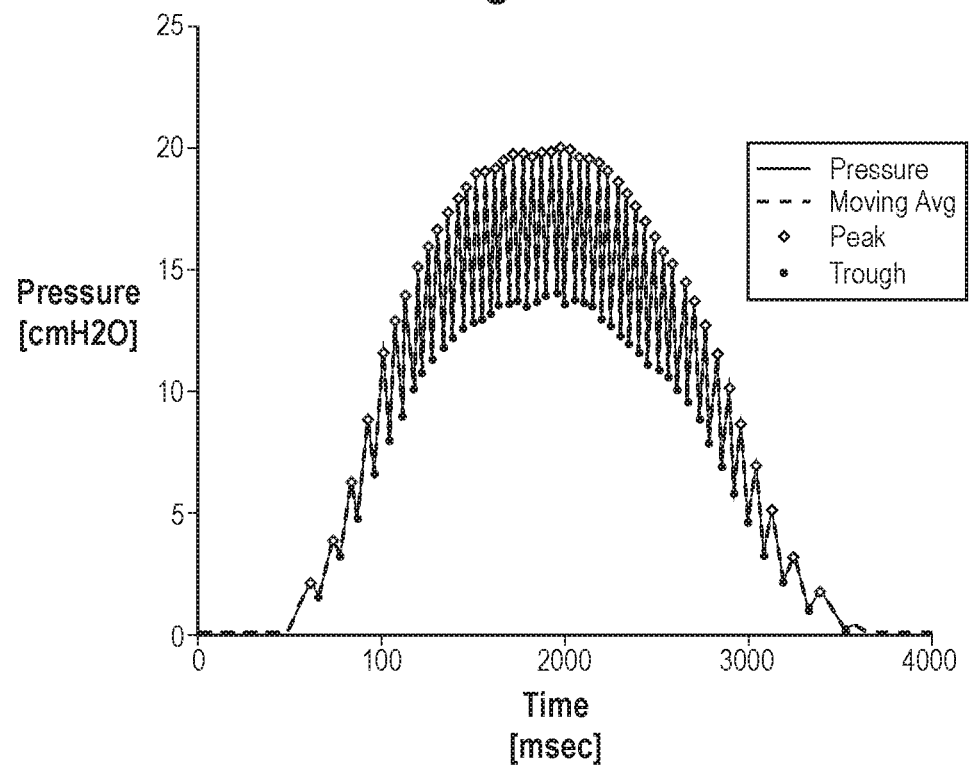
FIGS. 46A and B are exemplary graphs of pressure v. time data gathered from a smart OPEP device.
Figure 46B:
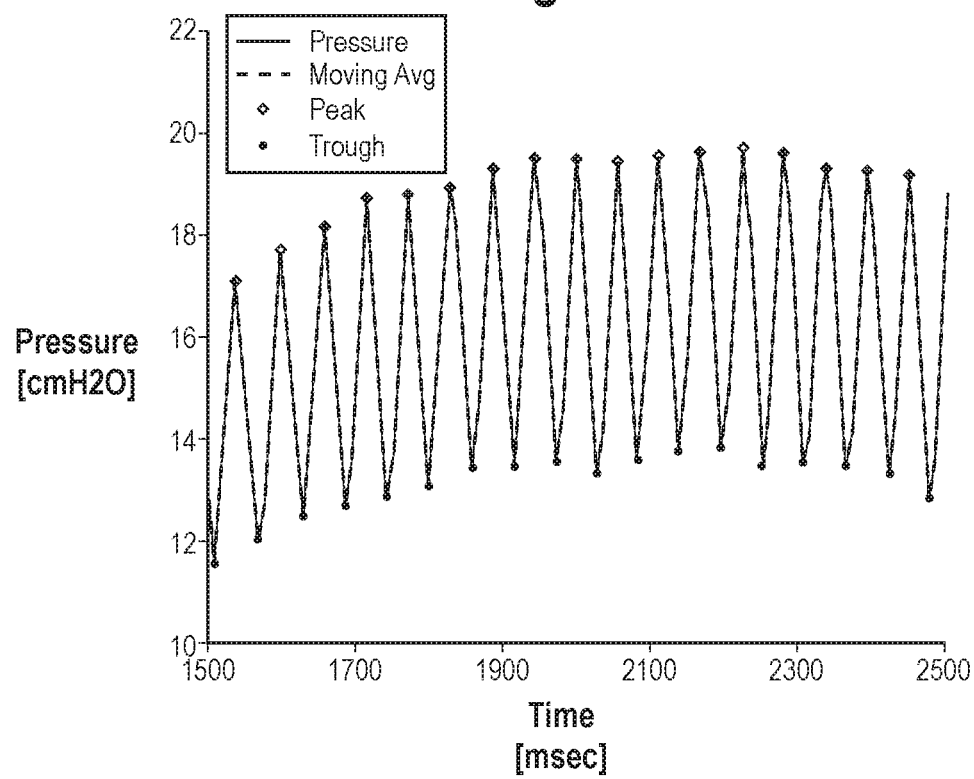

Referring to FIG. 31, the algorithm for calculating the performance characteristics including recording the raw data, filtering or smoothing the raw data to remove any noise, which may be accomplished by known techniques including a moving average, Butterworth filter, Fourier filter or Kernel filter. The direction of the slope is determined using the filtered/smoothed data, whether positive or negative. Slope changes between positive and negative are identified and labelled as a peak, with changes from negative to positive labeled as a trough. For each peak and trough, the timestamp and pressure value is logged. Exemplary data is shown in FIGS. 46A and B. Using the time and pressure value for each peak and trough, the frequency, amplitude and mean pressures are calculated.

Figure 23:
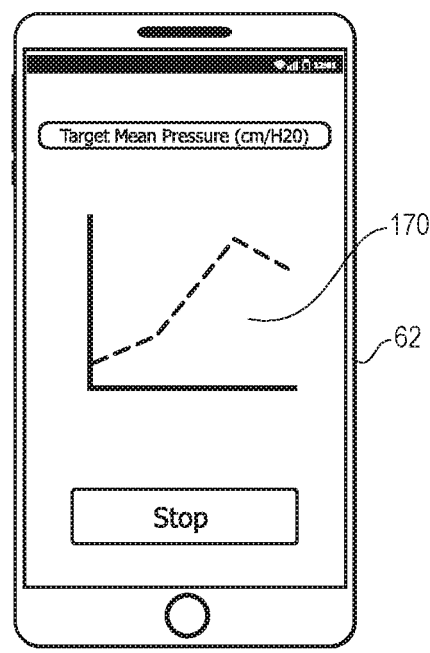
FIG. 23 is a view of a user interface with an output screen.
Figure 30:
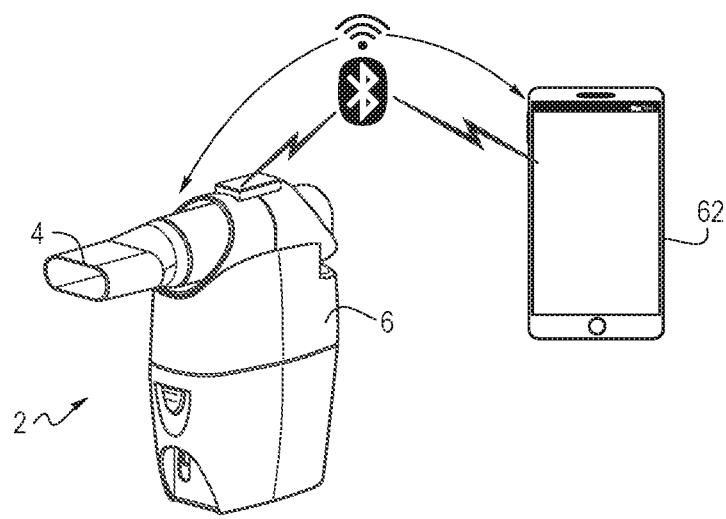
FIG. 30 is a schematic of a system with an OPEP device communicating with a user interface via a wireless protocol.
Figure 32:
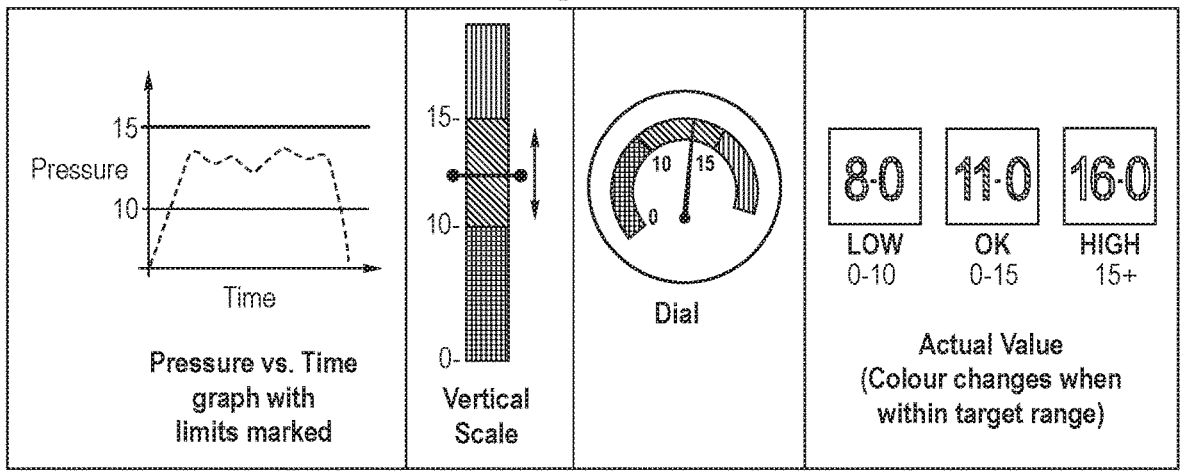
FIG. 32 are examples of output screens for a user interface.

The computing device, such as a mobile device including a smartphone 62, may function as the output device (and also the manual input (auxiliary input component) and analysis source). In these examples, the Smart OPEP communicates with the smartphone via a wireless protocol such as Bluetooth as shown in FIG. 30. An application (app) will allow the user to input the desired performance characteristic and set the limits if necessary (FIG. 21). An output screen 170 will display the target limits and provide feedback to the user (e.g., too high, too low, or ok) as shown in FIGS. 21, 23 and 32.

Figure 33:
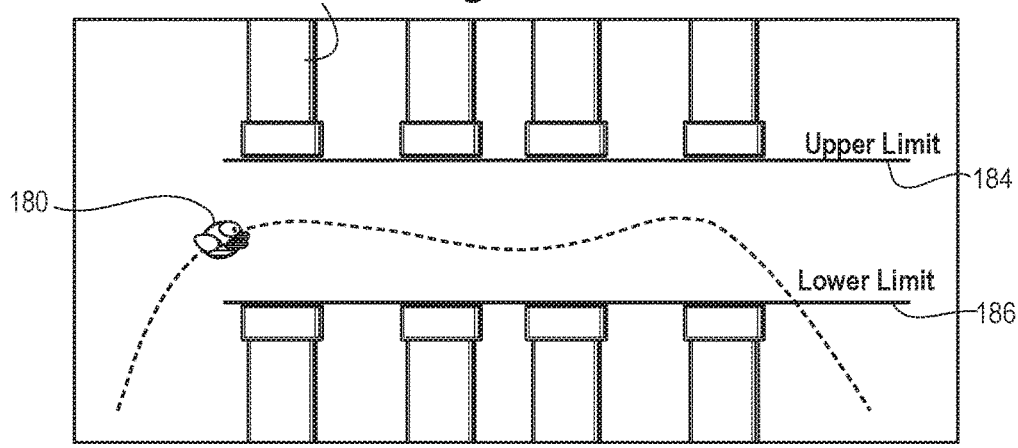
FIG. 33 is a view of a user interface with one embodiment of an output game.
Figure 34:
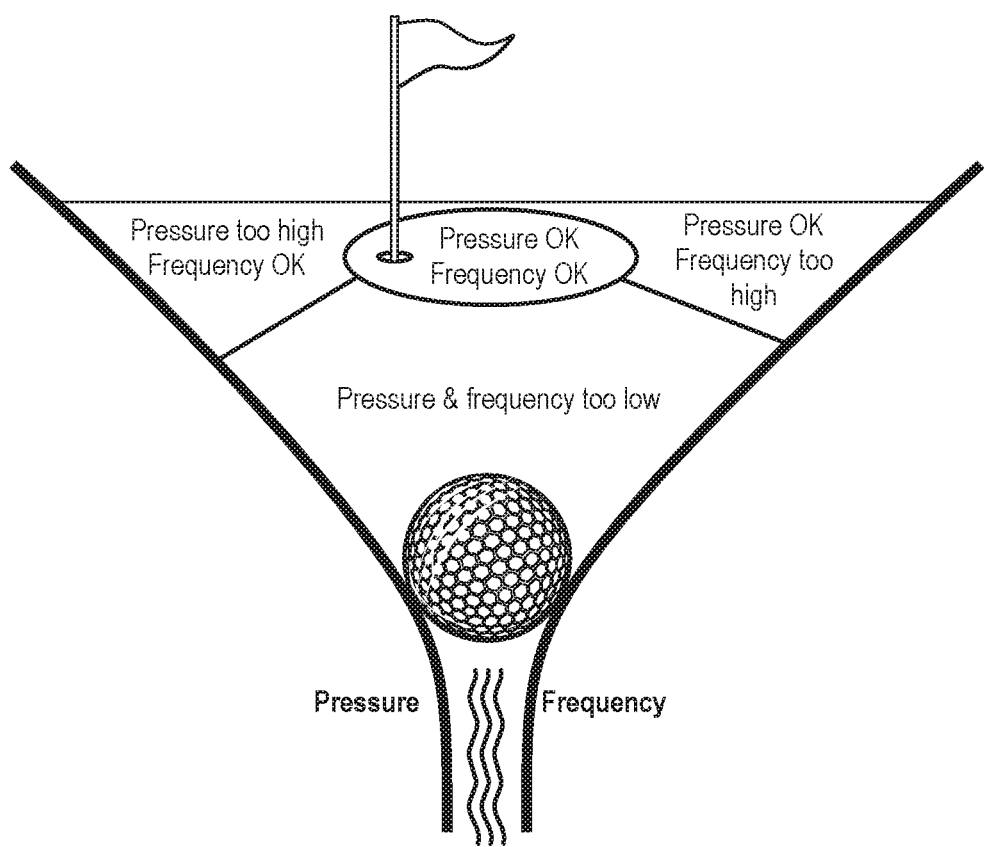
FIG. 34 is a view of a user interface with one embodiment of an output game providing feedback on pressure and frequency.

Referring to FIGS. 33 and 34, another possible output for this feature may be to turn the session into a game. For example, and referring to FIG. 33, the bird 180 represents the current performance characteristic value, which must pass through the pipes 182 without going outside the limits (upper and lower) 184, 186. If both frequency and pressure targets are required, care must be taken to ensure that the user is not overwhelmed with the feedback and is able to compensate their breathing technique to meet the required targets. A custom output graphic could be developed to aid the user in controlling two performance characteristics, such as frequency and pressure. FIG. 34 illustrates an example of a simple game that helps aid the user in controlling both frequency and pressure. The goal of the game is to get the ball into the hole and the current location of the ball is dependent on the frequency and pressure.

Figure 45:
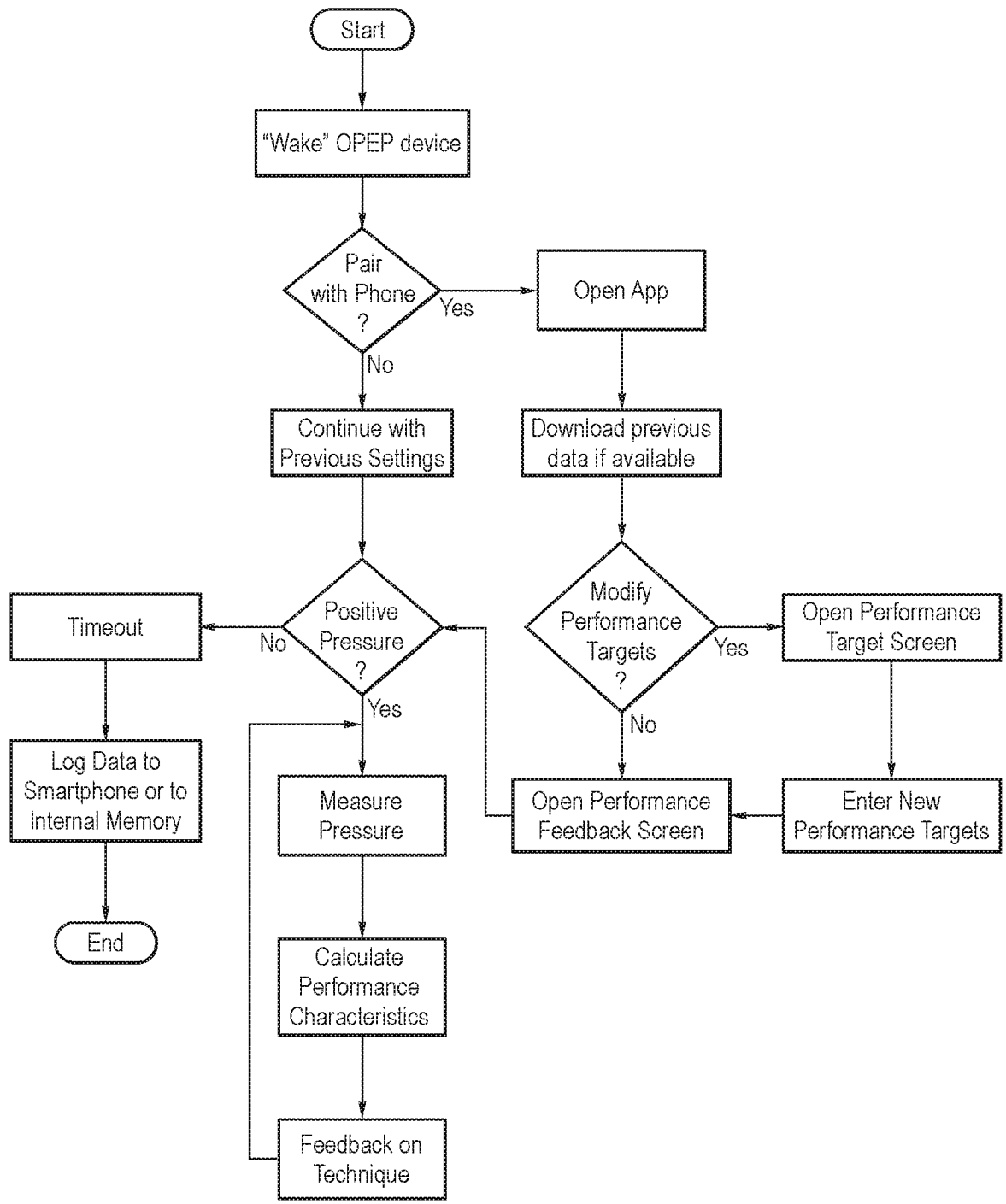
FIG. 45 is a flow chart of a treatment sequence using a smart OPEP system.

Referring to FIG. 45, to start a therapy session, the user first wakes the OPEP device, for example by pushing a manual button or automatically as the device is picked up by using an accelerometer. Once awake, the device pairs with a mobile device, such as a smart phone, if available. If a mobile device is available, an application may be opened and any previous data saved in memory may be downloaded in the mobile device. The user may be prompted to modify performance targets if desired. Once performance targets are set, the application opens the feedback screen so that the user may monitor their performance throughout the treatment. If a smart phone is not available, the previous performance targets are used, and the data is saved internally. The OPEP device begins monitoring for positive pressure. If at any point during treatment, the device does not detect a positive pressure change for a specified amount of time, the device saves any treatment data to either the mobile device or the internal memory and enters a standby mode to conserve power. If positive pressure is detected, the OPEP device will begin to measure the pressure (positive and negative), calculate the performance characteristics such as frequency, amplitude and mean pressures and provide feedback to the user regarding their technique.

One aspect of the embodiments disclosed herein relates to the handling of data. Data logged by the OPEP may be transferred to an external device, such as a smartphone, tablet, personal computer, etc. If such an external device is unavailable, the data may be stored internally in the OPEP in a data storage module or other memory and transferred upon the next syncing between the OPEP and external device. Software may accompany the OPEP to implement the data transfer and analysis.

In order to provide faster and more accurate processing of the data, for example from one or more various sensors, generated within the smart OPEP, data may be wirelessly communicated to a smart phone, local computing device and/or remote computing device to interpret and act on the raw sensor data.

In one implementation, the smart OPEP includes circuitry for transmitting raw sensor data in real-time to a local device, such as a smart phone. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the smart OPEP.

In addition to simply presenting data, statistics or instructions on a display of the smart phone or other local computer in proximity of the smart OPEP, proactive operations relating to the smart OPEP may be actively managed and controlled. For example, if the smart phone or other local computer in proximity to the smart OPEP determines that the sensor data indicates the end of treatment has been reached, or that further treatment is needed, the smart phone or other local computing device may communicate such information directly to the patient. Other variations are also contemplated, for example where a remote server in communication with the smart phone, or in direct communication with the smart OPEP via a communication network, can supply the information and instructions to the patient/user.

In yet other implementations, real-time data gathered in the smart OPEP and relayed via to the smart phone to the remote server may trigger the remote server to track down and notify a physician or supervising caregiver regarding a problem with the particular treatment session or a pattern that has developed over time based on past treatment sessions for the particular user. Based on data from the one or more sensors in the smart OPEP, the remote server may generate alerts to send via text, email or other electronic communication medium to the user, the user's physician or other caregiver.

Figure 49:
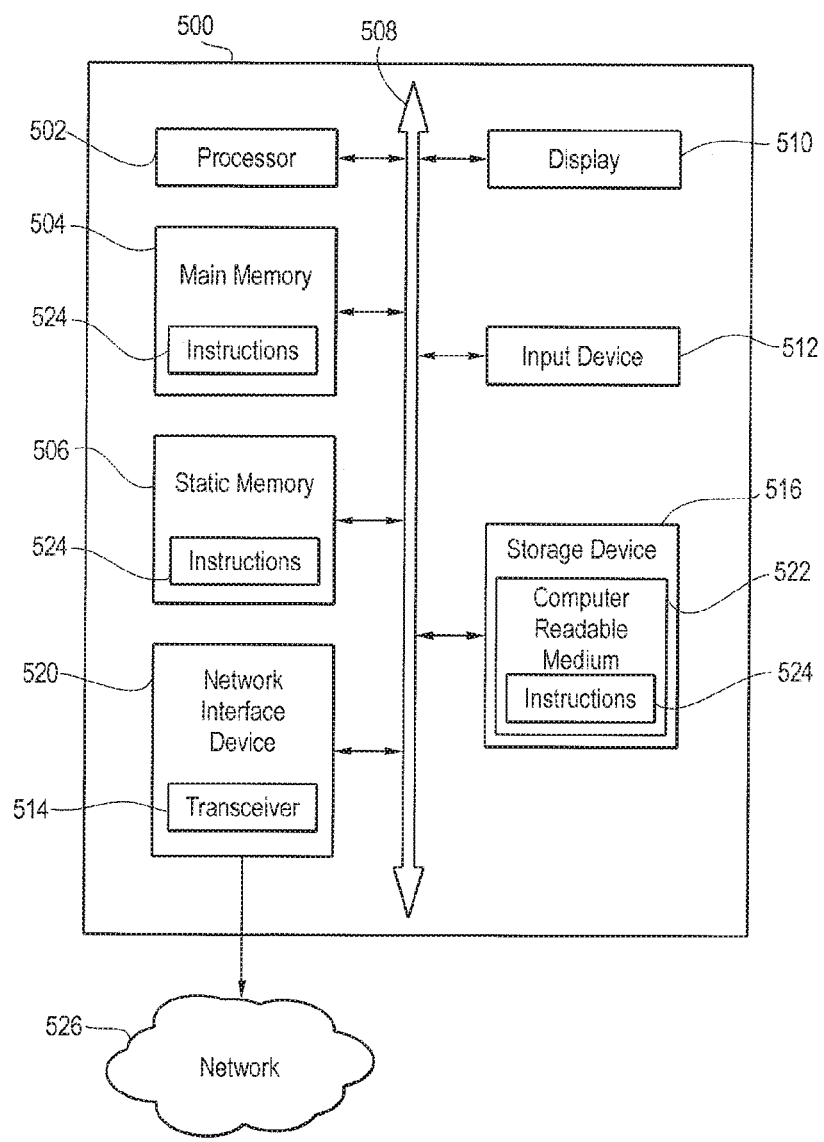
FIG. 49 is a schematic illustrating the computer structure.

The electronic circuitry in the smart OPEP (e.g. the controller arrangement of FIGS. 4 and 44), the local computing device and/or the remote server discussed above, may include some or all of the capabilities of a computer in communication with a network and/or directly with other computers. As illustrated in FIGS. 49 and 50, the computer 500 may include a processor 502, a storage device 516, a display or other output device 510, an input device 512, and a network interface device 520, all connected via a bus 508. A battery 503 is coupled to and powers the computer. The computer may communicate with the network. The processor 502 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor 502 executes instructions and includes that portion of the computer 500 that controls the operation of the entire computer. Although not depicted in FIGS. 49 and 50, the processor 502 typically includes a control unit that organizes data and program storage in memory and transfers data and other information between the various parts of the computer 500. The processor 502 receives input data from the input device 512 and the network 526 reads and stores instructions (for example processor executable code) 524 and data in the main memory 504, such as random access memory (RAM), static memory 506, such as read only memory (ROM), and the storage device 516. The processor 502 may present data to a user via the output device 510.

Although the computer 500 is shown to contain only a single processor 502 and a single bus 508, the disclosed embodiment applies equally to computers that may have multiple processors and to computers that may have multiple busses with some or all performing different functions in different ways.

The storage device 516 represents one or more mechanisms for storing data. For example, the storage device 516 may include a computer readable medium 522 such as read-only memory (ROM), RAM, non-volatile storage media, optical storage media, flash memory devices, and/or other machine-readable media. In other embodiments, any appropriate type of storage device may be used. Although only one storage device 516 is shown, multiple storage devices and multiple types of storage devices may be present. Further, although the computer 500 is drawn to contain the storage device 516, it may be distributed across other computers, for example on a server.

The storage device 516 may include a controller (not shown) and a computer readable medium 522 having instructions 524 capable of being executed on the processor 502 to carry out the functions described above with reference to processing sensor data, displaying the sensor data or instructions based on the sensor data, controlling aspects of the smart OPEP to alter its operation, or contacting third parties or other remotely located resources to provide update information to, or retrieve data from those remotely located resources. In another embodiment, some or all of the functions are carried out via hardware in lieu of a processor-based system. In one embodiment, the controller is a web browser, but in other embodiments the controller may be a database system, a file system, an electronic mail system, a media manager, an image manager, or may include any other functions capable of accessing data items. The storage device 516 may also contain additional software and data (not shown), which is not necessary to understand the invention.

The output device 510 is that part of the computer 500 that displays output to the user. The output device 510 may be a liquid crystal display (LCD) well-known in the art of computer hardware. In other embodiments, the output device 510 may be replaced with a gas or plasma-based flat-panel display or a traditional cathode-ray tube (CRT) display. In still other embodiments, any appropriate display device may be used. Although only one output device 510 is shown, in other embodiments any number of output devices of different types, or of the same type, may be present. In one embodiment, the output device 510 displays a user interface. The input device 512 may be a keyboard, mouse or other pointing device, trackball, touchpad, touch screen, keypad, microphone, voice recognition device, or any other appropriate mechanism for the user to input data to the computer 500 and manipulate the user interface previously discussed. Although only one input device 512 is shown, in another embodiment any number and type of input devices may be present.

The network interface device 520 provides connectivity from the computer 500 to the network 526 through any suitable communications protocol. The network interface device 520 sends and receives data items from the network 526 via a wireless or wired transceiver 514. The transceiver 514 may be a cellular frequency, radio frequency (RF), infrared (IR) or any of a number of known wireless or wired transmission systems capable of communicating with a network 526 or other smart devices 102 having some or all of the features of the example computer of FIGS. 83 and 84. The bus 508 may represent one or more busses, e.g., USB, PCI, ISA (Industry Standard Architecture), X-Bus, EISA (Extended Industry Standard Architecture), or any other appropriate bus and/or bridge (also called a bus controller).

The computer 500 may be implemented using any suitable hardware and/or software, such as a personal computer or other electronic computing device. The computer 500 may be a portable computer, laptop, tablet or notebook computers, smart phones, PDAs, pocket computers, appliances, telephones, and mainframe computers are examples of other possible configurations of the computer 500. The network 526 may be any suitable network and may support any appropriate protocol suitable for communication to the computer 500. In an embodiment, the network 526 may support wireless communications. In another embodiment, the network 526 may support hard-wired communications, such as a telephone line or cable. In another embodiment, the network 526 may support the Ethernet IEEE (Institute of Electrical and Electronics Engineers) 802.3x specification. In another embodiment, the network 526 may be the Internet and may support IP (Internet Protocol). In another embodiment, the network 526 may be a LAN or a WAN. In another embodiment, the network 526 may be a hotspot service provider network. In another embodiment, the network 526 may be an intranet. In another embodiment, the network 526 may be a GPRS (General Packet Radio Service) network. In another embodiment, the network 526 may be any appropriate cellular data network or cell-based radio network technology. In another embodiment, the network 526 may be an IEEE 802.11 wireless network. In still another embodiment, the network 526 may be any suitable network or combination of networks. Although one network 526 is shown, in other embodiments any number of networks (of the same or different types) may be present.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or use the processes described in connection with the presently disclosed subject matter, e.g., through the use of an API, reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations. Although exemplary embodiments may refer to using aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be spread across a plurality of devices. Such devices might include personal computers, network servers, and handheld devices, for example.

Providing feedback to users regarding their technique is one feature of the smart OPEP that will help optimize treatment. A controller, which may be located on or inside the various embodiments of the smart OPEP described herein, is in communication with one or more sensors, switches and or gauges that are tracking or controlling operation of the smart OPEP. The controller may store data gathered in a memory, integrated into the controller or implemented as a discrete non-volatile memory located in the smart OPEP, for later download to a receiving device, or may transmit data to a receiving device in real-time. Additionally, the controller may perform some processing of the gathered data from the sensors, or it may store and transmit raw data. RF transmitter and/or receiver modules may be associated with the controller on the smart OPEP to communicate with remote hand-held or fixed computing devices in real-time or at a later time when the smart OPEP is in communication range of a communication network to the remote hand-held or fixed location computing devices. The controller may include one or more of the features of the computer system 500 shown in FIG. 83. Additionally, the one or more sensors, switches or gauges may be in wired or wireless communication with the controller.

For clarity in displaying other features of the various Smart OPEP embodiments described, the controller circuitry is omitted from some illustrations, however a controller or other processing agent capable of at least managing the routing or storing of data from the smart OPEP is contemplated in one version of these embodiments. In other implementations, the smart OPEP may not include an onboard processor and the various sensors, gauges and switches of a particular embodiment may wirelessly communicate directly with a remotely located controller or other processing device, such as a handheld device or remote server. Data gathered by a controller or other processing device may be compared to expected or pre-programmed values in the local controller memory or other remote location to provide the basis for feedback on whether desired performance or therapy is taking place. If the controller is a more sophisticated and includes more of the computer 500 elements described in FIG. 49, then this processing may all be local to the smart OPEP. In more rudimentary controller arrangements, the data may simply be date/time stamped, and may also be appended with a unique device ID, and stored locally or remotely for later processing. In one embodiment, the data may further be locally or remotely stamped with a unique device or patient identifier.

Feature: Performance Limits

Figure 35:
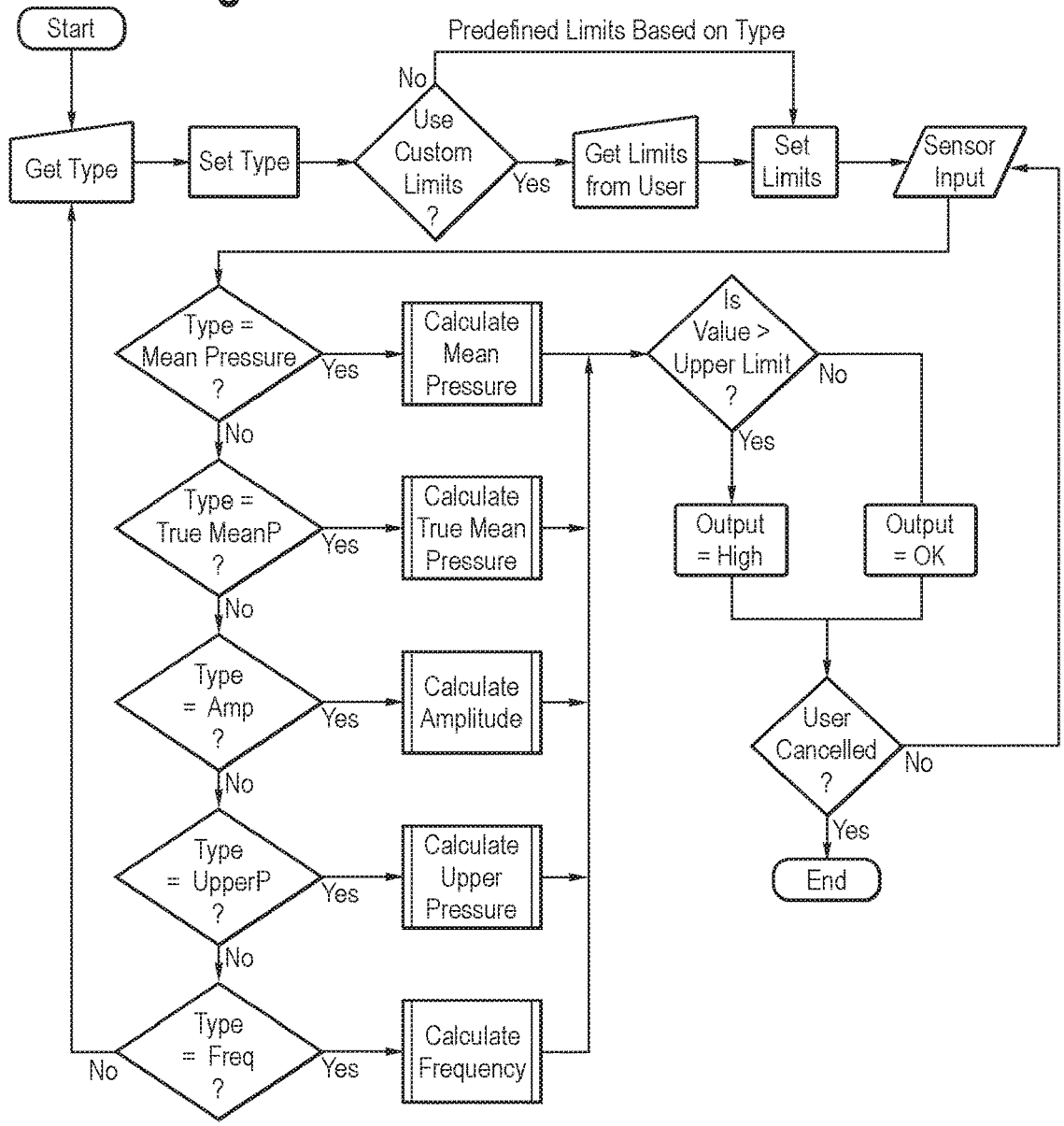
FIG. 35 is a flow chart for performance limits.

Referring to FIG. 35, the patient or HCP may be notified if a pressure characteristic is exceeded. The main purpose for this feature is to ensure patient safety and is a simplified version of the previous feature. For example, OPEP therapy is used post-operatively and patients may need to remain below a certain pressure. The flow chart in FIG. 35 is similar to the flow chart of FIG. 25, but only contains an upper limit. Any of the outputs discussed above may be used in this feature, such as visual, audible, vibration, or a smartphone display.

Feature: Real-Time DFP Feedback

Previous features may only inform the user if the input is high, low, or acceptable. An additional feature provides quantitative real-time feedback of the desired performance characteristic.

All of the inputs listed in the previous features can be used for this feature:
 10.2.1. Pressure Sensor
 10.2.2. Flex Sensor
 10.2.3. Non-contact Position Sensor
 10.2.4. LVDT
 10.2.5. Conductive Membrane
 10.2.6. Hall Effect Sensor
 10.2.7. Light Curtain
 10.2.8. Flow Sensor
 10.2.9. Potentiometer Vane
 10.2.10. Piezo Flex Sensor
 10.2.11. LED/Photo Sensor
 10.2.12. Proximity Sensor
 10.2.13. Accelerometer
 10.2.14. Microphone The inputs can be analyzed to determine:
 10.3.1. Peak and valley detection
 10.3.2. Average peak
 10.3.3. Average valley
 10.3.4. Amplitude
 10.3.5. Mean pressure
 10.3.6. True mean pressure
 10.3.7. Frequency In order to display the DFP in real-time, a computer device, such as a laptop, smartphone, or tablet, or other separate device with a display is required.

Feature: DFP History

Another feature provides a way for the patient or HCP to review DFP data from previous sessions. DFP data can be displayed over time and the user can retrieve and display the data by some temporal component, including for example and without limitation day, week, month, year, or all time. This allows the user to quickly visualize trends in the performance.

Feature: Ensure Proper Setting

This feature provides feedback to the user regarding the appropriate resistance setting. In one embodiment, the OPEP device provides five (5) resistance settings which change the frequency, amplitude and mean pressure performance. For a given flow rate, increasing the resistance setting increases the frequency and pressure characteristics. In one embodiment, for example the Aerobika® OPEP device IFU, the correct resistance setting will produce an Inspiratory:Expiratory ratio (I:E ratio) of 1:3 or 1:4 for 10-20 min without excess fatigue. Therefore, the input will be used to identify the start and end of the inspiratory and expiratory cycles. Some possible inputs include a flow sensor, pressure sensor, or microphone.

A flow sensor may be placed in the mouthpiece and used to determine the I:E ratio. A single flow sensor, placed at location 1 in FIG. 36, would need to be able to measure flow in both directions. It would also be possible to use two (2) one-way flow sensors: one in the location 1 for exhalation and one in location 2, as shown in FIG. 36, for inhalation.

A pressure sensor may be used to calculate the I:E ratio. If the pressure is negative then the flow is inspiratory, and if the pressure is positive then the flow is expiratory. The pressure sensor may be positioned as shown in FIG. 24.

Figure 36:
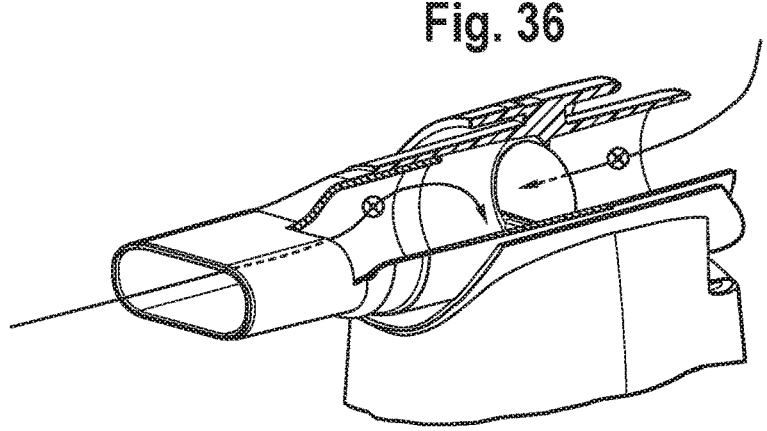
FIG. 36 is a partial, perspective view of an OPEP device with dual flow sensors.

In an alternative embodiment, two (2) microphones may to be used for the calculation of the I:E ratio, similar to the dual flow sensors shown in FIG. 36. A single microphone would only be able to identify if flow is occurring, and not if it is inspiratory or expiratory.

Figure 37:
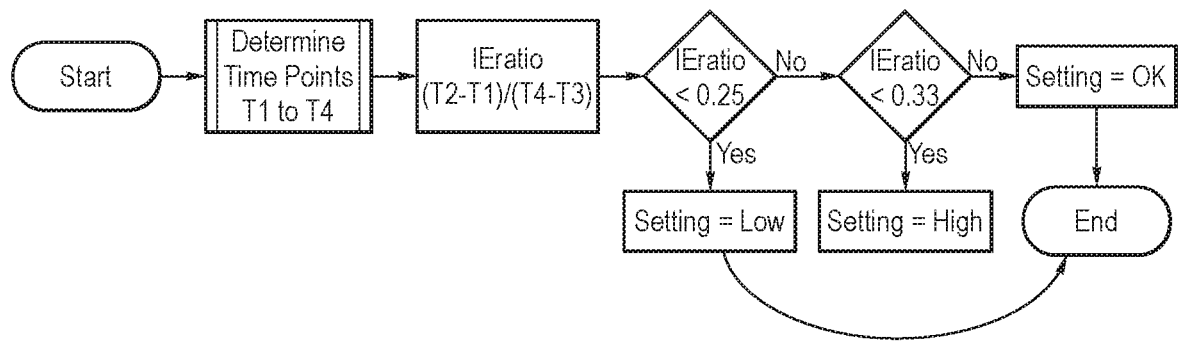
FIG. 37 is a flow chart for analyzing an I:E ratio.
Figure 38:
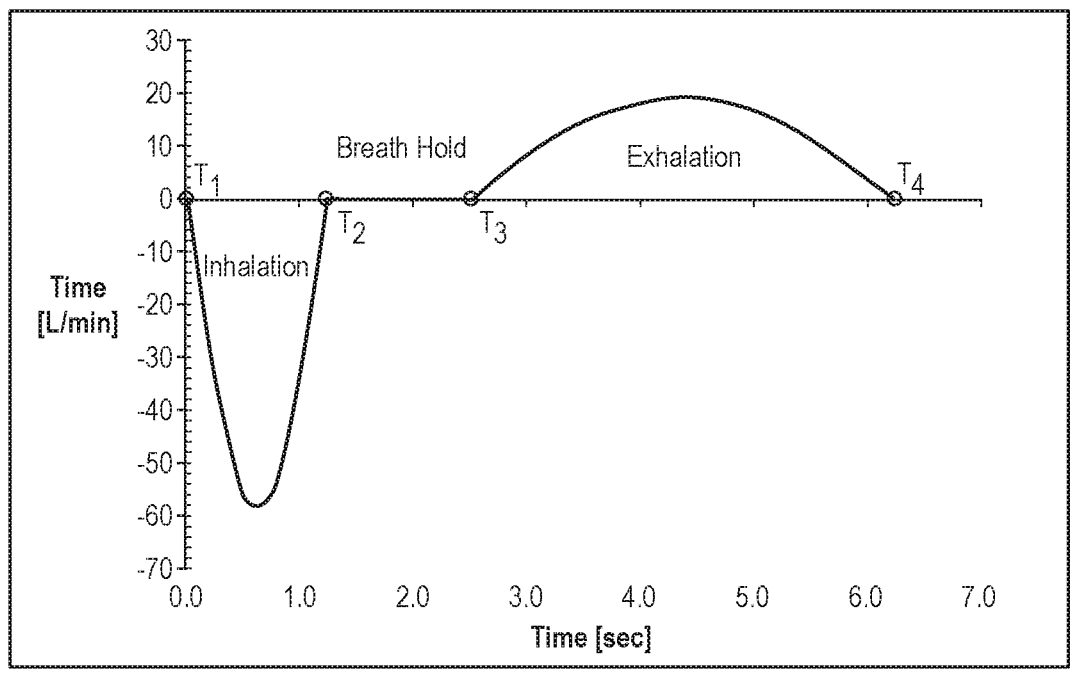
FIG. 38 is a graph showing an I:E ratio.

To analyze the I:E ratio, four (4) time points need to be determined: the start and end of inhalation (T1 and T2), and the start and end of exhalation (T3 and T4). The analysis could follow the logic shown in FIG. 37. If two (2) sensors are used, additional logic is required to determine if the flow is inspiratory or expiratory.

Figure 27:
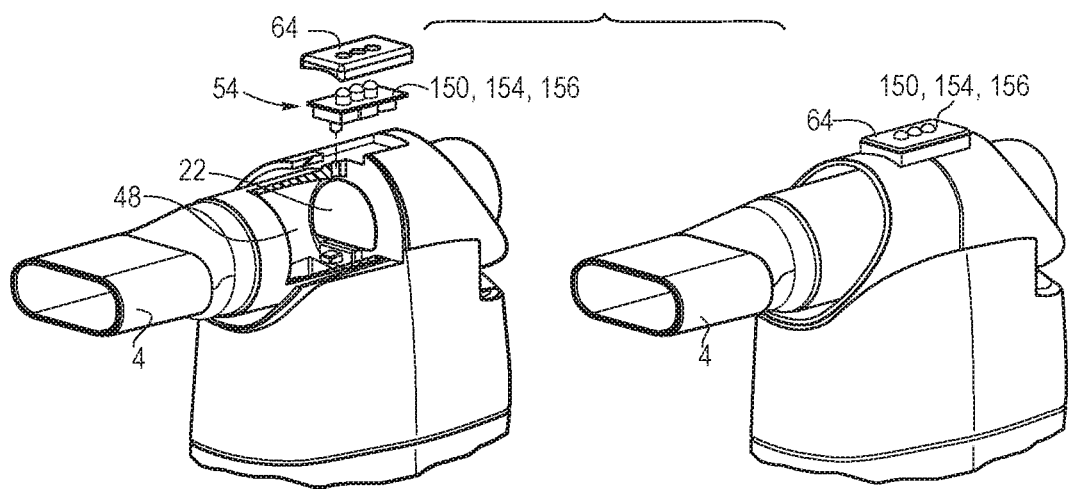
FIG. 27 shows partial exploded and non-exploded views of an OPEP device with an LED output.
Figure 28:
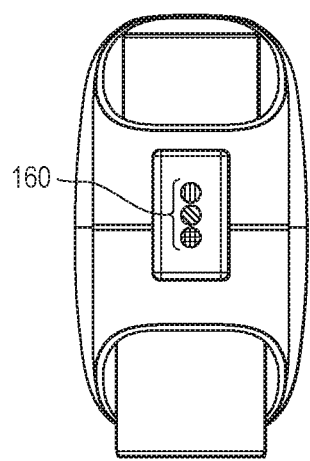
FIG. 28 is a view of an LED output.
Figure 29:
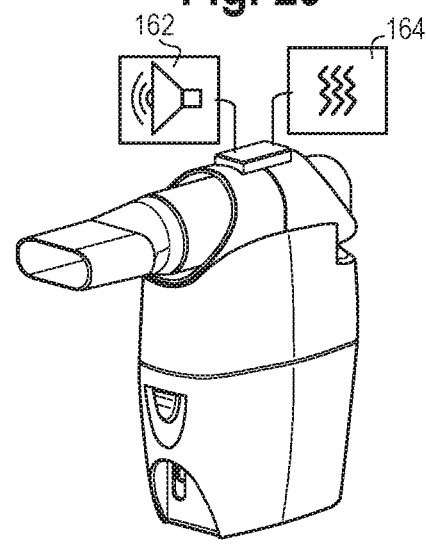
FIG. 29 is perspective view of an OPEP device with an auditory or vibratory/tactile output.

If Sensor 1 is ON and Sensor 2 is OFF
Then flow is expiratory
If Sensor 1 is ON and Sensor 2 is ON
Then flow is inspiratory The output of this feature would make recommendations to the user to either increase resistance, decrease resistance, or leave the resistance setting unchanged. An output component may be embedded in the device and be either visual, audible, or tactile as shown in FIGS. 27-28, or, the output may be shown on a separate device such as a smartphone, or other computer device or screen.

Feature: Setting Recommendation Based on Previous Data

This feature will analyze previous DFP data and make setting recommendations. This feature may calculate the I:E Ratio for each breath and then calculate the average I:E Ratio for a session. Based on the average I:E Ratio, this feature would make a setting change recommendation using the logic shown in FIG. 37 and/or referred to above.

Feature: Proper Technique

This feature will provide the user with training and coaching on proper technique for performing an OPEP maneuver based on the IFU, and may be updated for other devices. In one embodiment, this feature may take the form of an app, and will communicate with the OPEP device via BTLE (see FIG. 4 for more details).

A proper OPEP maneuver relies on several variables, such as I:E Ratio, frequency, pressure, and setting. These inputs have been previously discussed.

The ideal OPEP maneuver follows these steps: Inhale slowly, taking a deeper breath than normal but not filling the lungs, hold your breath and exhale actively. To analyze the first step, the app needs to learn the user's breathing pattern. This is done during the initial setup or training session and could be re-evaluated if the user's performance changes. To start, the user would inhale normally through the device in order to calculate their baseline inspiratory pressure, or IPTidal, or Tidal Volume (TV). Next, the user would inhale fully through the device to calculate their maximum inspiratory pressure, or $IP_{max}$, or Inspiratory Capacity (IC). The app would then calculate the target inspiratory pressure ($IP_{target}$) or volume for step #1 which is more than $IP_{tidal}$ (or the Tidal Volume) and less than the $IP_{max}$ (or Inspiratory Capacity). A starting point for the $IP_{target}$ (or target inspiratory volume) would be the average of $IP_{tidal}$ and $IP_{max}$ (or the TV and the IC).

The Next Step Involves Holding Your Breath for 2-3 Seconds. Breath Hold=T3-T2.

Next, the user exhales actively, but not forcefully. Frequency and pressures should be within target range and exhalation should last 3-4 times longer than inhalation. Exhaling actively is a subjective description of the OPEP maneuver, therefore, the app will calculate the frequency, mean pressure and I:E ratio in real-time, and use that information and data to determine if the proper technique is being achieved.

The output of this coaching feature will guide the user toward the correct OPEP technique based on the user's breathing pattern and specific performance targets. If any of steps above are not performed correctly, the app will make suggestions to change the user's technique. For example, if the user doesn't hold their breath before exhaling, the app would offer a reminder. In another example, the app may suggest that the user increase their flow rate because the mean pressure is too low and is not within the accepted limits. To declare the user "trained", the app may require the user to demonstrate a proper OPEP maneuver several times. The app could also play audio of a proper OPEP maneuver, which may assist the user in exhaling actively. The app may also include training videos explaining the proper technique and examples of people performing proper OPEP maneuvers. The app may also notify the user's healthcare provider (HCP) if proper technique isn't being completed.

Feature: Session Assist

In addition to the coaching feature, the Smart OPEP device can assist the user in following the correct therapy regime. Session Assist features aid the user or HCP in completing an OPEP session. For the first time user, an OPEP session can be confusing and complicated. The user needs to count the number of breaths, remember proper technique, remember when to perform 'Huff' coughs, and etc. For example, the the Aerobika® OPEP device IFU recommends the following steps: perform 10-20 OPEP maneuvers or breaths, after at least 10 breaths, perform 2-3 'Huff' coughs, repeat for 10-20 minutes twice/day on a regular base, increase to 3-4 times/day if needed.

Using the inputs defined earlier, this feature would count the number of breaths and provide feedback to the user, either with the number remaining or the number completed. The app would then remind the user to perform 'Huff' coughs after the appropriate number of breaths, and then repeat the breath counting/huff cough cycle for 10-20 minutes. The user may input the total number of breaths to complete or total session time as a goal and track progress. The Session Assist feature would also track the number of sessions per day, which can be used to determine the user's progress or quality of life.

Feature: Quality of Life Score

This feature transforms quantitative data into qualitative data that is easier for the user, HCP, or payer to understand. There are three (3) steps involved: determine the user's Quality of Life (QoL) score, correlate past DFP performance to QoL score, and predict QoL score based on DFP performance trends. Various inputs may be used to calculate a QoL score which will be correlated with DFP performance. Inputs may be both qualitative and quantitative. Algorithms may be tailored or adjusted for different disease types. Some examples of QoL inputs are: St. George's Respiratory questionnaire for COPD, simplified questionnaire, user's journal, steps/day, and/or number of hours the user is sedentary.

The objective is to calculate a QoL score that evolves over time as the user's condition improves or worsens. Initially, the user completes a questionnaire and a baseline QoL score is computed. The user's journal would be scanned for keywords such as: good day, bad day, cough, out of breath, etc., and the QoL score would be adjusted based on the number of times keywords appear (i.e good day=+1, out of breath=−1). The application may also calculate (or integrate with another app or device such as a FitBit) the number of steps taken per day and use this information to adjust the QoL score.

Figure 39:
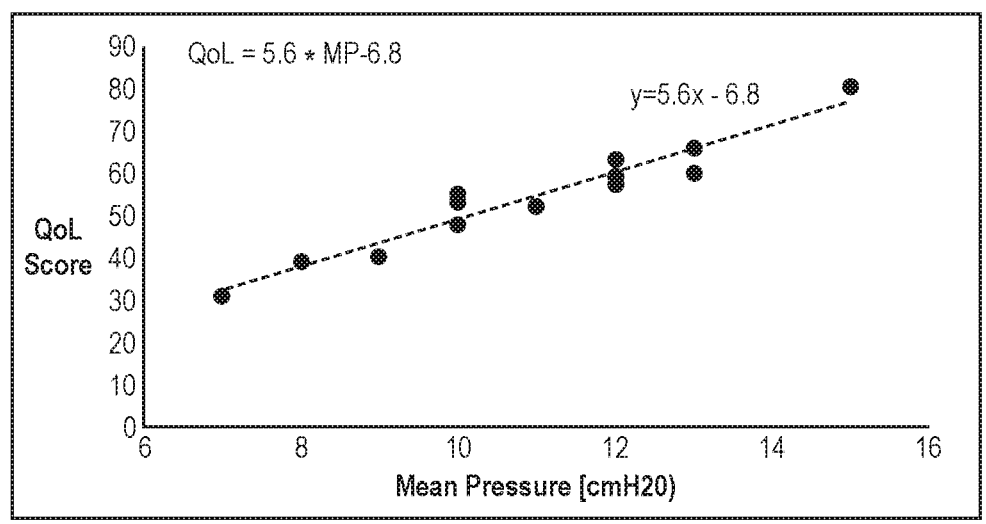
FIG. 39 is a graph showing the linear regression of mean pressure v. QoL score.
Figure 40:
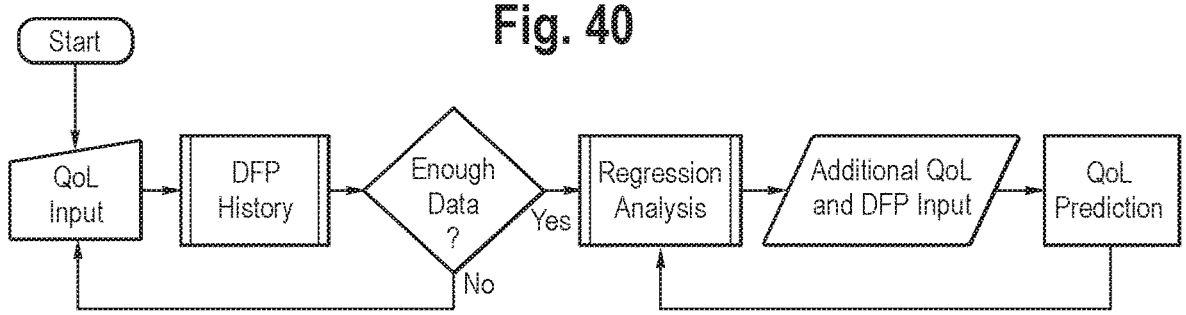
FIG. 40 is a flow chart for determining a relationship between a QoL score and measurements taken from the OPEP device.

Once a QoL score has been generated, the app would determine a relationship between the QoL score and the measurements in the DFP history. This would require a period of time when the app is 'learning' how the two (2) variables relate. In the following example, after one week of OPEP sessions (2×/day) and daily QoL input from the user, the following linear regression equation is defined: QoL=5.6×MP-6.8 as shown in FIG. 39. A linear regression equation may also be calculated for each of the other measurable and the equations with the highest "m" magnitude (y=mx+b) would be used to predict the QoL score. For example, if the Frequency/Qol equation was: QoL=1.2F+5.2 it would indicate that, for this particular user, changes in frequency would be less likely to indicate a change in QoL than changes in Mean Pressure. A flow chart for this feature is shown in FIG. 40. Outputs for this feature include: current and previous QoL score, suggestions improve QoL score, measureable vs. QoL score and linear regression results, encouragement when QoL score decrease, and/or notification to HCP when QoL score decreases.

Feature: Device Status

This feature provides feedback to the user about the device itself. Several options exist, including notifying the user, HCP or payer that the device needs to be replaced. This may take the form of a reminder in the app, or could lockout features until a new lot number or serial number is entered. The feedback may also include notifying the user when the device needs to be cleaned. Cleaning notifications could be based on the number of sessions between cleaning or changes in device performance over time.

Feature: Stakeholder Updates

A stakeholder is defined as an individual or organization, outside the patient's immediate family, that has an interest in the patient's condition, treatment, and progress. Stakeholders may be the patient's doctor, respiratory therapists, hospital, or insurance company. Some examples of stakeholder updates include: updating an insurance company with the user's usage data to monitor patient adherence and/or updating HCP with user's progress since last visit, usage data, and QoL score.

Feature: Active OPEP

Figure 41:
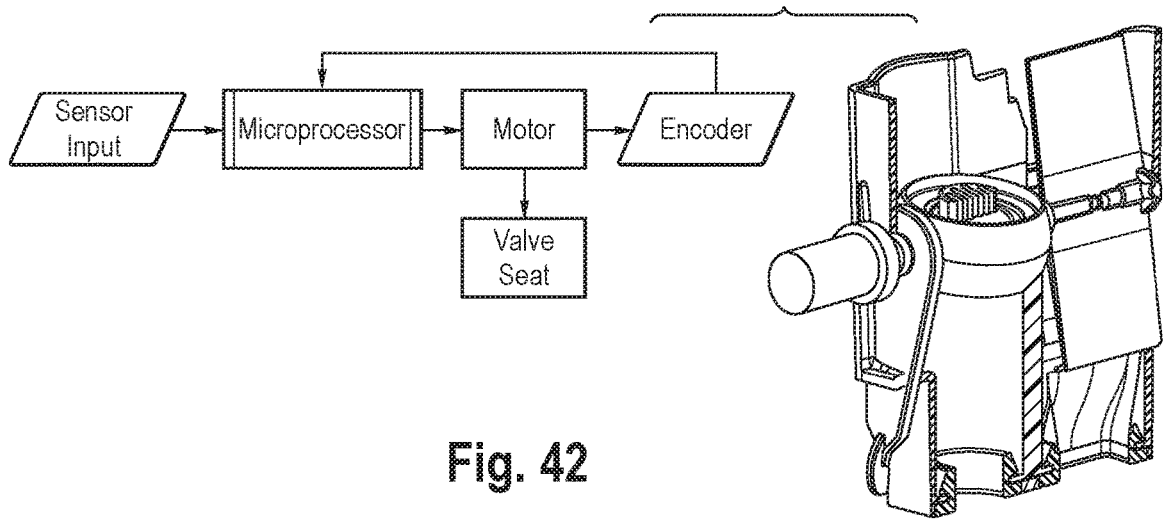
FIG. 41 is a flow chart and partial cross-sectional view of an active OPEP device.

Referring to FIG. 41, a device is disclosed that automatically adjusts the resistance to keep the selected performance characteristic (e.g., pressure (amplitude) and/or frequency) in the desired range. The range and/or performance characteristic to be controlled may be pre-programmed into the device or be inputted by the user as described above. The microprocessor would receive data from the sensor and an algorithm would decide how to adjust the device. The microprocessor would then give a command to a motor 190 and the motor would physically perform the adjustment of a control component, such as the valve seat 148 or orientation of the chamber inlet. The encoder 192 would confirm the position of the motor and provide that information back to the microprocessor. This would improve user adherence since all the user needs to do is exhale into the device. The device will automatically set and control the resistance setting to achieve the desired therapy. Another option would be to program into the algorithm variations in frequency or pressure as some research has shown to be beneficial.

Feature: Lung Health

Figure 42:
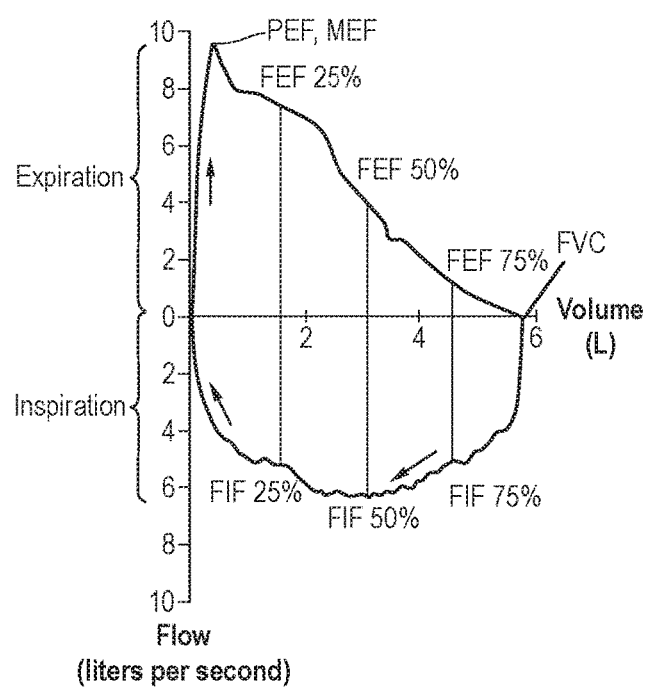
FIG. 42 is a graph of a flow-volume loop.

Referring to FIG. 42, one embodiment includes a flow sensor, which makes it possible to evaluate the patient's lung health by turning off the oscillations and allowing the device to operate like a spirometer. The flow sensor would need to be able to measure flow in both directions (inspiratory and expiratory). An algorithm take the flow being measured and generate a flow-volume (FV) loop shown below in FIG. 42. From the FV Loop, various parameters may be calculated and fed back to the patient.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An oscillating positive expiratory pressure system comprising:
   an oscillating positive expiratory pressure device comprising a first chamber defining in part an exhalation flow path, and a second chamber isolated from the first chamber;
   a base component having a first thickness;
   a flexible connector surrounding the base component and moveably connecting the base component to the oscillating positive expiratory pressure device, wherein the flexible connector has a second thickness less than the first thickness, wherein the flexible connector and base component separate the first and second chambers;
   a pressure sensor in communication with the second chamber, wherein the pressure sensor is operative to sense a pressure in the second chamber and generate an input signal correlated to the pressure;
   a processor operative to receive the input signal from the pressure sensor and generate an output signal; and
   a visual output, wherein the visual output is operative to receive the output signal, and wherein the visual output displays an output.

2. The oscillating positive expiratory pressure system of claim 1 further comprising an audible output operative to receive the output signal.

3. The oscillating positive expiratory pressure system of claim 1 further comprising a vibratory output operative to receive the output signal.

4. The oscillating positive expiratory pressure system of claim 1 wherein the visual output comprises a graphical user interface.

5. The oscillating positive expiratory pressure system of claim 1 wherein the visual output comprises a mobile device in wireless communication with the oscillating positive expiratory pressure device.

6. The oscillating positive expiratory pressure system of claim 5 wherein the mobile device comprises an auxiliary input component.

7. The oscillating positive expiratory pressure system of claim 6 wherein the mobile device comprises the processor.

8. The oscillating positive expiratory pressure system of claim 5 wherein the mobile device displays an output graphic responsive to one or both of frequency and pressure.

9. The oscillating positive expiratory pressure system of claim 5 wherein the mobile device further comprises an auxiliary input component configured to input quality of life information.

10. The oscillating positive expiratory pressure system of claim 1 wherein the pressure sensor comprises a displacement sensor.

11. The oscillating positive expiratory pressure system of claim 10 wherein the flexible connector comprises a bellows connecting the base component to the oscillating positive expiratory pressure device, wherein the base component is moveable toward and away from the displacement sensor.

12. The oscillating positive expiratory pressure system of claim 11 further comprising a spring disposed in the second chamber between the base component and the displacement sensor.

13. The oscillating positive expiratory pressure system of claim 10 wherein the displacement sensor comprises a light curtain.

14. The oscillating positive expiratory pressure system of claim 1 wherein the base component is planar.

15. An oscillating positive expiratory pressure system comprising:
   an oscillating positive expiratory pressure device comprising a first chamber defining in part an exhalation path, and a second chamber isolated from the first chamber;
   a base component having a first thickness;
   a flexible connector surrounding the base component and moveably connecting the base component to the oscillating positive expiratory pressure device, wherein the flexible connector has a second thickness less than the first thickness, wherein the flexible connector and base component separate the first and second chambers;
   a control component operative to control a flow resistance;
   a pressure sensor in communication with the second chamber, wherein the pressure sensor is operative to sense a pressure in the second chamber and generate an input signal correlated to the pressure;
   a processor operative to receive the input signal from the pressure sensor and generate an output signal; and
   an output component operative to receive the output signal, and adjust the control component to provide a predetermined flow resistance.

16. The oscillating positive expiratory pressure system of claim 15 wherein the control component comprises a valve component.

17. The oscillating positive expiratory pressure system of claim 16 wherein the output component comprises a motor coupled to the valve component.

18. The oscillating positive expiratory pressure system of claim 17 further comprising an encoder coupled to the motor.

19. The oscillating positive expiratory pressure system of claim 15 wherein the pressure sensor comprises a displacement sensor.

20. The oscillating positive expiratory pressure system of claim 19 wherein the flexible connector comprises a bellows connecting the base component to the oscillating positive expiratory pressure device, wherein the base component is moveable toward and away from the displacement sensor.

21. The oscillating positive expiratory pressure system of claim 20 further comprising a spring disposed in the second chamber between the base component and the displacement sensor.

22. The oscillating positive expiratory pressure system of claim 19 wherein the displacement sensor comprises a light curtain.

23. The oscillating positive expiratory pressure system of claim 15 wherein the base component is planar.

24. A method of using an oscillating positive expiratory pressure system comprising:
   exhaling into a first chamber of an oscillating positive expiratory pressure device and thereby creating a first pressure;
   controlling a flow resistance in the first chamber with a control component during the exhaling;
   moving a base component having a first thickness by applying the first pressure to the base component during the exhaling and flexing a flexible connector connected between the base component and the oscillating positive expiratory pressure device, wherein the flexible connector has a second thickness less than the first thickness, and thereby applying a second pressure in a second chamber isolated from the first chamber;
   sensing the second pressure in the second chamber during the exhaling with a pressure sensor in communication with the second chamber;
   generating an input signal correlated to the second pressure;
   receiving the input signal with a processor and generating an output signal;
   receiving the output signal with an output component; and
   adjusting the control component with the output component to vary the flow resistance in response to the output signal.

25. The method of claim 24 wherein the control component comprises a valve component.

26. The method of claim 24 wherein the output component comprises a motor coupled to the valve component.

* * * * *